(12) United States Patent
Arishima et al.

(10) Patent No.: US 8,335,148 B2
(45) Date of Patent: Dec. 18, 2012

(54) POLYMERIZABLE COMPOUND, POLYMERIZABLE COMPOSITION, OPTICAL MATERIAL, OPTICAL ELEMENT AND OPTICAL HEAD DEVICE

(75) Inventors: Hiroyuki Arishima, Koriyama (JP); Hiroki Hotaka, Koriyama (JP)

(73) Assignee: Asahi Glass Company, Limited, Tokyo (JP)

( * ) Notice: Subject to any disclaimer, the term of this patent is extended or adjusted under 35 U.S.C. 154(b) by 8 days.

(21) Appl. No.: 13/156,719

(22) Filed: Jun. 9, 2011

(65) Prior Publication Data

US 2011/0310721 A1    Dec. 22, 2011

(30) Foreign Application Priority Data

Jun. 17, 2010  (JP) .................. 2010-138624

(51) Int. Cl.
*G11B 7/00*   (2006.01)
(52) U.S. Cl. .................................. 369/112.01
(58) Field of Classification Search ........................ None
See application file for complete search history.

(56) References Cited

FOREIGN PATENT DOCUMENTS
| | | |
|---|---|---|
| JP | 2004-315744 | 11/2004 |
| JP | 2005-298665 | 10/2005 |
| WO | WO 2009/139476 A1 | 11/2009 |

*Primary Examiner* — Paul Huber

(74) *Attorney, Agent, or Firm* — Oblon, Spivak, McClelland, Maier & Neustadt, L.L.P.

(57) ABSTRACT

A polymerizable compound represented by the following formula (1):

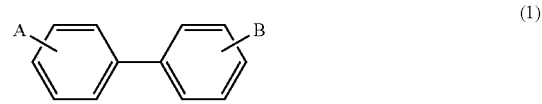

(1)

wherein A is a hydrogen atom or a group selected from the following formulae (2) to (5):

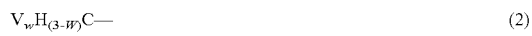

(2)

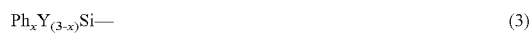

(3)

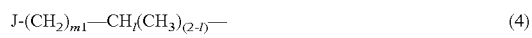

(4)

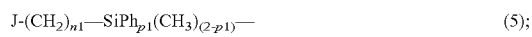

(5);

B is a group selected from the following formulae (6) and (7):

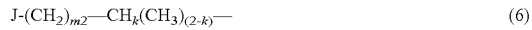

(6)

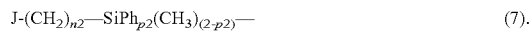

(7).

13 Claims, 5 Drawing Sheets

-1st order diffracted light    0th order light    +1st order diffracted light

0th order light

−1st order diffracted light   +1st order diffracted light
0th order light

−1st order diffracted light   +1st order diffracted light
0th order light

POLYMERIZABLE COMPOUND, POLYMERIZABLE COMPOSITION, OPTICAL MATERIAL, OPTICAL ELEMENT AND OPTICAL HEAD DEVICE

BACKGROUND OF THE INVENTION

1. Field of the Invention

The present invention relates to a novel polymerizable compound having a biphenyl skeleton, a polymerizable composition comprising the polymerizable compound, an optical material using the polymerizable composition, an optical element using the optical material, and an optical head device.

2. Discussion of Background

Resin materials having a high refractive index are widely used as optical materials, since optical elements may thereby be made to be small-sized or to have high efficiency. Specifically, they are used, for example, for display panels, eyeglass lenses, optical disks or optical filters.

In recent years, in such applications, it has been promoted to increase the light intensity or to shorten the wavelength to be used, and accordingly, it has been required to improve the light resistance of the high refractive index resin materials.

In a case where an optical material such as a high refractive index resin material is inferior in the light resistance, if such an optical material is used as a component or an element, a decrease in the transmittance or an increase in the optical strain is likely to occur as the time passes, and it becomes difficult to use it stably over a long period of time.

The above requirement is particularly distinct in the field of optical disks. For example, pits are formed by convexoconcaves provided on the surface of an optical disk such as CD (compact disk) or DVD (digital versatile disk). Information recorded in pits can be read by irradiating the optical disk surface with a laser light and detecting its reflected light by an optical head device. In recent years, in order to increase the capacity of an optical disk, it has been promoted to further shorten the wavelength of the laser light and to further reduce the pit size on the optical disk. For example, a system may be proposed wherein a laser light having a wavelength of from 300 to 450 nm (hereinafter referred to also as a blue laser light) is employed as a light source, and particularly BD (blu-ray disk) is remarkably growing in recent years.

An optical material to be used for such an optical head device is required to have not only high light resistance but also a high refractive index. For example, a polarization hologram element is used as a polarization separation element for an optical head device and has a structure wherein a birefringent resin and an isotropic resin are laminated. In the case of the polarization hologram element, the refractive index in ordinary ray direction or the refractive index in extraordinary ray direction of the birefringent resin is made to be substantially equal to the refractive index of the isotropic resin, in order to improve the polarization characteristics and the diffraction efficiency.

However, a high refractive index material usually has a large wavelength dispersion of the refractive index, and the absorption for short wavelength light tends to be large. Accordingly, in a case where a birefringent resin having a high refractive index of at least 1.55 is used for example, light resistance of the isotropic resin having a high refractive index matching therewith is not sufficient, and there has been a problem that deterioration in the transmittance is likely to occur.

Further, in the case of the after-mentioned wavelength-selective diffraction element, a material having a small wavelength dispersion of the refractive index (hereinafter referred to as a low wavelength dispersion property) and a material having a large wavelength dispersion of the refractive index (hereinafter referred to as large wavelength dispersion property) are laminated to form a diffraction grating.

In such a case, the larger the wavelength dispersion property of the large wavelength dispersion material, the more the wavelength-selective diffraction index difference with the low wavelength dispersion material can be made and the more the grating height can be reduced, whereby characteristics preferred in view of the production process and the diffraction efficiency will be obtained.

However, the large wavelength dispersion material is usually required to have an absorption band at the long wavelength side, and is likely to be inferior in the light resistance, like the above-described high refractive index material.

As the high refractive index resin material to be used as an optical material, heretofore, a compound having a skeleton of e.g. fluorene, tetraphenylmethane, 1,1,2,2-tetraphenylethane or biphenyl has been proposed (Patent Documents 1 and 2).

In the case of the compounds disclosed in Patent Documents 1 and 2, it is possible to improve the light resistance of the resin material to a certain extent by increasing the number of polymerizable groups in the molecule, by adding a light stabilizer, or by another means. However, even in such a case, sufficient light resistance is hardly obtainable, and further improvement in the light resistance is required.

On the other hand, Patent Document 3 discloses a silicon compound as a material which can satisfy both high refractive index and high light resistance. However, even the silicon compound disclosed in Patent Document 3 has insufficient light resistance and wavelength dispersion property, and it is required to improve the wavelength dispersion property while high light resistance is maintained.

However, a high refractive index and high light resistance, or large wavelength dispersion property and high light resistance, tend to conflict with each other, and it has been difficult to improve both of them. Further, it has been more difficult to improve all of the high refractive index, the large wavelength dispersion property and high light resistance to satisfactory levels.

PRIOR ART DOCUMENTS

Patent Documents

Patent Document 1: JP-A-2004-315744

Patent Document 2: JP-A-2005-298665

Patent Document 3: WO2009-139476

SUMMARY OF THE INVENTION

Under these circumstances, it is an object of the present invention to provide a polymerizable compound having a high refractive index and large wavelength dispersion property and having excellent light resistance.

Further, it is another object of the present invention to provide a polymerizable composition using the polymerizable compound, an optical material prepared by the polymerizable composition, an optical element using the optical material, and an optical head device.

The present invention provides a polymerizable compound represented by the following formula (1):

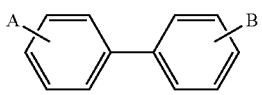

(1)

wherein A is a hydrogen atom or a group selected from the following formulae (2) to (5):

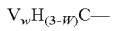             (2)

$V_w H_{(3-w)} C-$

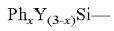             (3)

$Ph_x Y_{(3-x)} Si-$

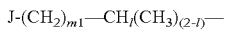             (4)

$J-(CH_2)_{m1}-CH_l(CH_3)_{(2-l)}-$

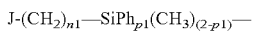             (5);

$J-(CH_2)_{n1}-SiPh_{p1}(CH_3)_{(2-p1)}-$

B is a group selected from the following formulae (6) and (7):

             (6)

$J-(CH_2)_{m2}-CH_k(CH_3)_{(2-k)}-$

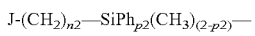             (7);

$J-(CH_2)_{n2}-SiPh_{p2}(CH_3)_{(2-p2)}-$ w is an integer of from 0 to 3;
V is a methyl group or an ethyl group, provided that when w is from 2 to 3, a plurality of V's may be different groups, x is an integer of from 0 to 3, Y is a group selected from a methyl group, a cyclohexyl group, a tert-butyl group, a sec-butyl group and an isopropyl group, provided that when x is 0 or 1, a plurality of Y's may be different groups, J is a group selected from $CH_2=CR-COO-$, an epoxy group, a vinyl group and a vinyl ether group, R is a hydrogen atom or a methyl group, I is an integer of from 0 to 1, k is an integer of from 0 to 2, provided that when A is a hydrogen atom, k is not 2, each of $m_1$ and $m_2$ which are independent of each other, is from 0 to 12, each of $n_1$ and $n_2$ which are independent of each other, is from 1 to 12, and each of $p_1$ and $p_2$ which are independent of each other, is from 0 to 2;
provided that some or all of hydrogen atoms in the substituent V in the formula (2), the phenyl group and the substituent Y in the formula (3) and the alkylene group in the formulae (4) to (7) may be substituted by a methyl group, a methoxy group or a fluorine atom, and some or all of hydrogen atoms in the biphenyl group or the biphenylene group may be substituted by a methyl group, a methoxy group or a fluorine atom.

In the polymerizable compound, A is preferably a group represented by the formula (3). Further, in the polymerizable compound, A is preferably a triphenylsilyl group. Further, in the polymerizable compound, it is preferred that A is a triphenylsilyl group, and B is a group represented by the formula (7).

Further, in the polymerizable compound, it is preferred that A is a group represented by the formula (5), and B is a group represented by the formula (7).

Further, in the polymerizable compound, it is preferred that when B is a group represented by the formula (6), k=0. Further, in the polymerizable compound, it is preferred that when B is a group represented by the formula (7), $p_2$=0.

Further, in the polymerizable compound, A is preferably a tert-butyl group. Further, in the polymerizable compound, it is preferred that each of $n_1$ and $n_2$ which are independent of each other, is from 1 to 3, and each of $m_1$ and $m_2$ which are independent of each other, is from 1 to 2.

Further, the present invention provides a polymerizable composition comprising the polymerizable compound represented by the above formula (1).

The present invention further provides an optical material obtained by curing the above polymerizable composition of the present invention.

The present invention further provides an optical element using the above optical material of the present invention.

The present invention still further provides an optical head device using the above optical element of the present invention.

According to the present invention, a polymerizable compound having a high refractive index and large wavelength dispersion property and having excellent light resistance, can be provided. Further, according to the present invention, by curing a polymerizable composition comprising the polymerizable compound of the present invention, an optical material having all of high refractive index, large wavelength dispersion property and high light resistance can be provided.

Further, according to the present invention, an optical element having excellent light resistance can be provided, and by using the optical element, an optical head device suitable for a large capacity can be provided.

DETAILED DESCRIPTION OF THE PREFERRED EMBODIMENTS

Figure 1A:
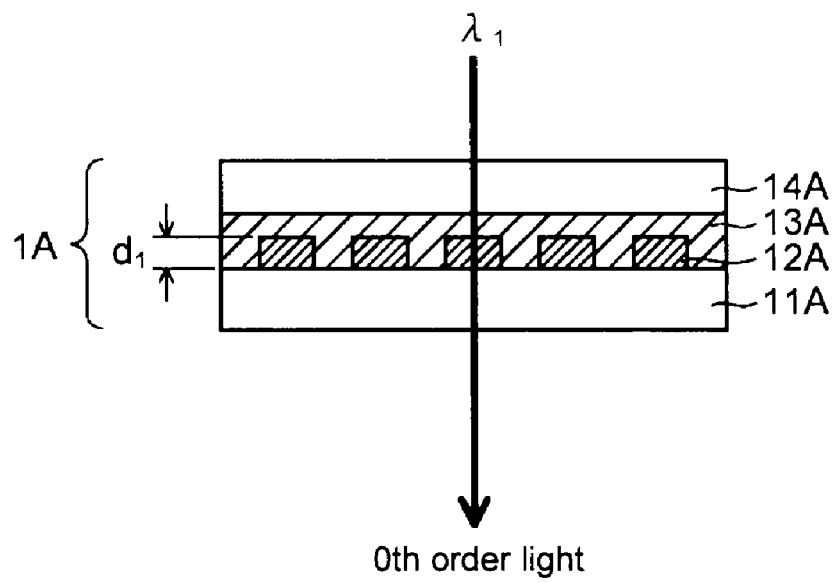
FIGS. 1(a) and 1(b) are cross-sectional views schematically illustrating a wavelength-selective diffraction element according to a first embodiment of the present invention.

In this specification, a compound represented by the formula (1) will be referred to as a compound (1). The same applies to other compounds.

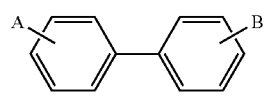

(1)

That is, the compound (1) of the present invention has a biphenylene skeleton as the main skeleton, and has a structure in which hydrogen atoms on the respective cyclic groups are substituted by A and B on the respectively different cyclic groups. By having the biphenylene skeleton as the main skeleton in such a manner, a high refractive index and large wavelength dispersion property can be obtained as compared with a compound having a single ring such as a phenyl group or a phenylene group as the main skeleton.

Here, in the formula (1), in a case where A is a hydrogen atom, the main skeleton in the formula (1) is "a biphenyl group", and in a case where A is a group other than the hydrogen atom, the main skeleton in the formula (1) is a "a biphenylene group".

Further, it was found that by the connecting atoms with the biphenyl group or the biphenylene group being a carbon atom or a silicon atom, and by at least one of such carbon atoms and silicon atoms being a tertiary or higher carbon atom or silicon atom, a high light resistance can be obtained as compared with a conventional compound having a biphenyl skeleton.

The substitution position in the biphenylene group by A or B is not particularly limited, and in a case where the biphenylene group is substituted at the 4-position or the 4'-position, the linearity of the compound (1) is increased, and the glass transition temperature of the resin is increased. Accordingly, the substitution position in the biphenylene group is preferably the 4-position or the 4'-position.

However, with a view to controlling the melting point or the refractive index of the compound (1), the biphenylene group may be substituted at the 2-position or the 2'-position. Further, in addition to A and B, some or all of hydrogen atoms bonded to the biphenyl group or the biphenylene group may be substituted by a methyl group, a ethoxy group or a fluorine atom.

In the formula (1), A is a hydrogen atom or a group selected from the following formulae (2) to (5):

$$V_w H_{(3-w)} C— \quad (2)$$

$$Ph_x Y_{(3-x)} Si— \quad (3)$$

$$J\text{-}(CH_2)_{m1}—CH_l(CH_3)_{(2-l)}— \quad (4)$$

$$J\text{-}(CH_2)_{n1}—SiPh_{p1}(CH_3)_{(2-p1)}— \quad (5)$$

In the formula (1), B is any one of groups of the following formulae (6) and (7):

$$J\text{-}(CH_2)_{m2}—CH_k(CH_3)_{(2-k)}— \quad (6)$$

$$J\text{-}(CH_2)_{n2}—SiPh_{p2}(CH_3)_{(2-p2)}— \quad (7)$$

The formula (2) is a group having hydrogen atoms of a methyl group substituted by substituents V, and V is a methyl group or an ethyl group.

Further, some or all of hydrogen atoms in the methyl group or the ethyl group may be substituted by a methyl group, a methoxy group or a fluorine atom within a range not to remarkably impair the light resistance, so as to adjust the melting point or the wavelength dispersion property.

In the formula (2), w is an integer of from 0 to 3, and with a view to improving the light resistance, w is preferably 3. When w is from 2 to 3, a plurality of V's may be the same group or different groups.

A group of the formula (3) comprising a silicon atom and a phenyl group and a substituent Y bonded to the silicon atom, and the substituent Y is selected from a methyl group, a cyclohexyl group, a tert-butyl group, a sec-butyl group and an isopropyl group. Among them, the substituent Y is preferably a cyclohexyl group or a tert-butyl group with a view to obtaining a higher light resistance. Further, some or all of hydrogen atoms in the methyl group, the cyclohexyl group, the tert-butyl group, the sec-butyl group and the isopropyl group as the substituent Y may be substituted by a methyl group, a methoxy group or a fluorine atom, and some or all of hydrogen atoms bonded to the carbon atoms of the phenyl group may be substituted by a methyl group, a methoxy group or a fluorine atom.

x is an integer of from 0 to 3, and with a view to securing a high refractive index and large wavelength dispersion property and further improving the light resistance, x is preferably from 2 to 3.

Here, when x is 0 or 1, a plurality of Y's may be the same group or different groups, but are preferably the same group from the viewpoint of availability of the materials and convenience in preparation.

In the formulae (4) to (7), J is a group selected from $CH_2=CR—COO—$, an epoxy group, a vinyl group and a vinyl ether group, and among them, $CH_2=CR—COO—$ is preferred, with which the photopolymerization reaction can be carried out in a short period of time, thus leading to excellent productivity.

In a case where an epoxy group is used as J, photopolymerization reaction by photocationic polymerization is possible, however, in general, the light resistance is decreased by a photo-initiator to be added for the polymerization. Further, in a case where J is an epoxy group, polymerization reaction by thermal polymerization is possible, but it may take long for the polymerization.

Accordingly, it is preferred to employ, as J, $CH_2=CR—COO—$ with which photo-radical polymerization is possible.

In $CH_2=CR—COO—$, R is a hydrogen atom or a methyl group, and specifically, when R is a hydrogen atom, $CH_2=CR—COO—$ is an acryloyloxy group, and when R is a methyl group, $CH_2=CR—COO—$ is a methacryloyloxy group.

In general, with an acryloyloxy group, the reaction quickly proceed as compared with a methacryloyloxy group. Accordingly, with a view to efficiently conducting the polymerization reaction, R is preferably hydrogen, that is, J is preferably an acryloyloxy group.

Further, it is possible to add, as additives, a known stabilizer such as a phenol antioxidant or a hindered amine light stabilizer to the polymerizable composition to stabilize the entire system. When J is an acryloyloxy group or a methacryloyloxy group, the type of a useful stabilizer is not limited very much, and accordingly it is possible to further improve light resistance by adding a stabilizer.

Further, in the formulae (4) to (7), in a case where J is $CH_2=CR—COO—$, some or all of hydrogen atoms in the alkylene group may be substituted by a methyl group, a methoxy group or a fluorine atom.

When A is a group represented by the above formula (4), $m_1$ is from 0 to 12, and is preferably from 1 to 2 with a view to maintaining the polymerizability and further maintaining a higher refractive index and a higher glass transition temperature.

When $m_1$ is 0, the polymerizability of the compound (1) may be impaired. On the other hand, if $m_1$ exceeds 3, the refractive index may be decreased, or the glass transition temperature may be decreased.

With a view to adjusting the refractive index of the compound (1), some or all of hydrogen atoms in $(CH_2)_{m1}$ in the formula (4) may be substituted by a methyl group, a methoxy group or a fluorine atom. Particularly when the hydrogen atom in $(CH_2)_{m1}$ is substituted by a fluorine atom, the wavelength dispersion property in a low refractive index region can be made larger, and accordingly it is possible to control the wavelength dispersion property of the compound (1) by the number of substitution by a fluorine atom. Further, some of methylene groups as $(CH_2)_{m1}$ may be substituted by oxygen.

With a view to further improving the light resistance, the carbon atom bonded to the biphenylene group preferably has at least one methyl group.

Accordingly, in the formula (4), although l is 0 or 1, l is preferably 0 with a view to improving the light resistance.

When A is a group represented by the above formula (5), this group is bonded to the biphenylene group by means of a silicon atom, and accordingly, the light resistance can be improved.

In the formula (5), $n_1$ is from 1 to 12, and is preferably from 1 to 3 with a view to obtaining a higher refractive index while maintaining a predetermined glass transition temperature.

If $n_1$ exceeds 4, the refractive index may be decreased, or the glass transition temperature may be decreased.

Further, with a view to adjusting the refractive index of the compound (1), some or all of hydrogen atoms in $(CH_2)_{n1}$ in the formula (5) may be substituted by a methyl group, a methoxy group or a fluorine atom. Particularly when the hydrogen atom in $(CH_2)_{n1}$ is substituted by a fluorine atom, the wavelength dispersion property in a low refractive index region can be made larger, and accordingly it is possible to control the wavelength dispersion property of the compound (1) by the number of substitution by a fluorine atom. Further, some of methylene groups as $(CH_2)_{n1}$ may be substituted by oxygen.

In the formula (5), $p_1$ is from 0 to 2, and with a view to obtaining a higher light resistance, $p_1$ is preferably 0. On the other hand, with a view to obtaining a higher refractive index, $p_1$ is preferably 2.

When B is a group represented by the formula (6), k is 0 to 2, and with a view to further improving the light resistance, the carbon atom bonded to the biphenyl group or the biphenylene group in B of the formula (6) preferably has at least one methyl group. That is, with a view to improving the light resistance, the carbon atom bonded to the biphenyl group or the biphenylene group is preferably tertiary or higher, and accordingly k is preferably 0 or 1, more preferably k is 0.

As described above, by the structure in which the carbon atom bonded to the biphenyl group or the biphenylene group has at least one methyl group, the light resistance can further be improved.

However, in a case where A is a hydrogen atom, k is 0 or 1. In a case where A is a hydrogen atom, if k is 2, the carbon atom bonded to the biphenyl group has no methyl group, and in this case, the light resistance of the compound (1) may not sufficiently be secured by e.g. a decrease in the glass transition temperature.

In the formula (6), $m_2$ is from 0 to 12, and with a view to maintaining the polymerizability and further maintaining a higher refractive index and a higher glass transition temperature, $m_2$ is preferably from 1 to 2.

In a case where $m_2$ is 0, the polymerizability of the compound (1) may be impaired. On the other hand, if $m_2$ exceeds 3, the refractive index may be decreased, or the glass transition temperature may be decreased.

With a view to adjusting the refractive index of the compound (1), some or all of hydrogen atoms in $(CH_2)_{m2}$ in the formula (6) may be substituted by a methyl group, a methoxy group or a fluorine atom. Particularly when the hydrogen atom in $(CH_2)_{m2}$ is substituted by a fluorine atom, the wavelength dispersion property in a low refractive index region can be made larger, and accordingly it is possible to control the wavelength dispersion property of the compound (1) by the number of substitution by a fluorine atom.

Further, some of methylene groups as $(CH_2)_{m2}$ may be substituted by oxygen.

When B is a group represented by the above formula (7), it is bonded to the biphenyl group or the biphenylene group by means of a silicon atom, and accordingly the light resistance can be improved.

In the formula (7), $n_2$ is from 1 to 12, and with a view to obtaining a higher refractive index while maintaining a predetermined glass transition temperature, $n_2$ is preferably from 1 to 3.

If $n_2$ exceeds 4, the refractive index may be decreased, or the glass transition temperature may be decreased.

With a view to adjusting the refractive index of the compound (1), some or all of hydrogen atoms in $(CH_2)_{n2}$ in the formula (7) may be substituted by a methyl group, a methoxy group or a fluorine atom.

Particularly when the hydrogen atom in $(CH_2)_{n2}$ is substituted by a fluorine atom, the wavelength dispersion property in a low refractive index region can be made larger, and accordingly it is possible to control the wavelength dispersion property of the compound (1) by adjusting the number of substitution by a fluorine atom.

Further, some of methylene groups as $(CH_2)_{n2}$ may be substituted by oxygen.

In the formula (7), $p_2$ is from 0 to 2, and with a view to obtaining a higher light resistance, $p_2$ is preferably 0. On the other hand, with a view to obtaining a higher refractive index, $p_2$ is preferably 2.

Among the groups represented by the formulae (2) to (5), A is preferably a group of the formula (3), whereby a high refractive index and large wavelength dispersion property can be obtained. Particularly, A is preferably a triphenylsilyl group.

That is, a compound represented by the following formula (8) (hereinafter referred to as a compound (8)) is preferred.

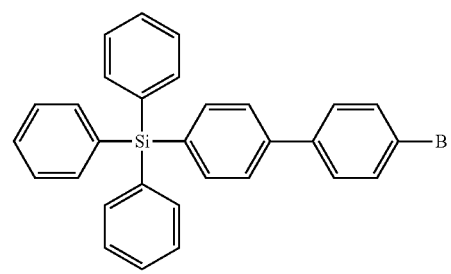

(8)

In the triphenylsilyl group, three phenyl groups having high polarizability are bonded to a silicon atom, and accordingly by bonding the triphenylsilyl group with the biphenylene group, a compound (1) can have a high refractive index and excellent light resistance and in addition, large wavelength dispersion property.

In the formula (8), B is represented by the formula (6) or (7), and with a view to increasing the light resistance, the atom bonded to the biphenylene group in the formula (8) is preferably a tertiary or higher carbon atom or silicon atom, more preferably a quaternary carbon atom or silicon atom.

Accordingly, in the formula (8), when B is a group represented by the formula (6), k is preferably 0.

Further, in the formula (8), when B is a group represented by the formula (7), with a view to making the melting point low, $p_2$ is preferably 0.

Further, among the compounds (1) of the present invention, preferred is one wherein A is a tert-butyl group. That is, a compound represented by the following formula (9) is preferred.

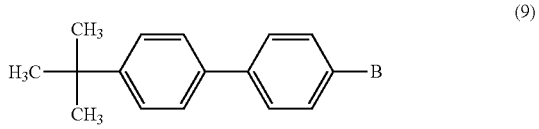

(9)

As shown in the formula (9), by bonding a tert-butyl group to the biphenylene group as the main skeleton, a sterically bulky molecular structure can be obtained, whereby a high glass transition temperature can be obtained, and high light resistance can be obtained when the compound is formed into an optical material.

In the formula (9), B is selected from the formulae (6) and (7), and with a view to increasing the light resistance, the atom bonded to the biphenylene group in the formula (9) is preferably a tertiary or higher carbon atom or silicon atom, more preferably a quaternary carbon atom or silicon atom.

Accordingly, when B is a group represented by the formula (6), k is preferably 0. Further, when B is a group represented by the formula (7), with a view to making the melting point low, $p_2$ is preferably 0.

Further, the compound (1) of the present invention is also preferably a compound wherein both A and B are a group having a polymerizable group, that is, A is a group of the formula (4) or (5), whereby a high light resistance is obtained.

With a view to further increasing the light resistance, the atom bonded to the biphenylene group in the formula (1) is preferably a tertiary or higher carbon atom or silicon atom, more preferably a quaternary carbon atom or silicon atom.

Accordingly, when A is a group represented by the formula (4), l is preferably 0. Further, when B is a group represented by the formula (6), k is preferably 0.

In the formula (1), in a case where both A and B have a polymerizable group, when a polymerizable composition containing such a compound is polymerized, crosslinked components are formed, and high light resistance can be obtained. On the other hand, when both A and B have a polymerizable group, polymerization shrinkage may proceed too much. Accordingly, when both A and B have a polymerizable group, it is preferred to properly adjust the amount of the compound (1).

Particularly, it is preferred that A is a group represented by the formula (5) and $p_1$ is 0, and B is a group represented by the formula (7) and $p_2$ is 0, whereby a low melting point and a high light resistance can be obtained.

The compound (1) of the present invention is preferably used as one component of the polymerizable composition.

The polymerizable composition may contain one type of the compound (1) as the polymerizable compound, or may contain two or more types of the compound (1). Further, the polymerizable composition may contain one or more types of the compound (I) and a polymerizable compound other than the compound (1) as mixed, and it may further contain a non-polymerizable compound.

A compound to be used for the polymerizable composition may properly be selected depending on the purpose of use, and for example, in a case where the polymerizable composition is used for application for which a high refractive index, a large wavelength dispersion property or high light resistance is required, the compound (8) having these properties is suitably used.

On the other hand, when the polymerizable composition is used for an application for which an operation property at low temperature is required, as a compound (1) having a low melting point, a compound wherein A is a group of the formula (5) and B is a group of the formula (7) is, for example, suitably used.

A polymerizable compound other than the compound (1) to be added to the polymerizable composition may be properly selected depending on the purpose of use from the viewpoint of the melting point, the viscosity, the refractive index, the wavelength dispersion property, etc., and is not particularly limited.

With a view to obtaining a resin having a high refractive index and excellent light resistance, the content of the compound (1) among polymerizable compounds contained in the polymerizable composition is preferably at least 10 mass %, more preferably at least 50 mass %.

The polymerizable composition of the present invention may contain reaction initiators to be used for the polymerization reaction. The polymerization reaction may, for example, be photopolymerization reaction or thermal polymerization reaction, and the photopolymerization reaction is preferably employed since polymerization reaction is possible with substantially no thermal influence over the peripheral members.

For the photopolymerization reaction, light rays such as ultraviolet rays or visible rays may be employed, and ultraviolet rays are particularly preferably employed since a high polymerization reaction rate is obtainable.

As a photopolymerization initiator, a known material may be employed. For example, one or more selected from acetophenones, benzophenones, benzoins, benzyls, Michler's ketones, benzoin alkyl ethers and benzyl dimethyl ketals may suitably be selected for use. The amount of the photopolymerization initiator is preferably from 0.05 mass % to 5 mass %, particularly preferably from 0.1 mass % to 2 mass %, based on the total amount of the composition.

Other components which may be incorporated to the polymerizable composition of the present invention may, for example, be ultraviolet absorbers, antioxidants and stabilizers such as light stabilizers. The amount of such other components is preferably at most 5 mass %, particularly preferably at most 2 mass %, based on the total amount of the polymerizable composition.

In the polymerizable composition of the present invention, an organic solvent may be contained. However, for the purpose of use for dilution of the composition, it is preferred to employ a low viscosity polymerizable compound rather than an organic solvent.

Further, in order to facilitate the handling at the time of polymerization, it is preferred to use the composition by heating it to a temperature within a range not to let it undergo thermal polymerization, to lower the viscosity.

By using the polymerizable compound of the present invention, an optical material having all of high refractive index, large wavelength dispersion property and light resistance can be obtained.

As described above, by curing the polymerizable composition containing the polymerizable compound of the present invention, particularly by photo-curing a photo-curable polymerizable composition, it is possible to obtain an optical material having all of high refractive index, large wavelength dispersion property and light resistance.

Further, according to the present invention, it is possible to provide an optical element using an optical material obtained by curing the polymerizable composition containing the polymerizable compound (1) of the present invention.

In general, an optical material having a refractive index of at least 1.55 cannot have excellent light resistance, and it has been difficult to obtain a refractive index of at least 1.55 with an optical material excellent in the light resistance. With the optical material of the present invention using the polymerizable compound (1), a high refractive index can be obtained, and accordingly it is preferably used for an application, for example, for which a refractive index of at least 1.55 at a wavelength of 589 nm is required. Further, with the optical material of the present invention, both high refractive index and high light resistance can be obtained, and accordingly the optical material of the present invention can suitably be used for an optical element for which such properties are required.

An optical element for which the optical material of the present invention is suitably used may, for example, be a polarization hologram element for which a refractive index $n_d$ of from 1.55 to 1.60 is required, or a wavelength-selective diffraction element for which a refractive index $n_d$ of from 1.60 to 1.70 is required. Further, the optical material of the present invention has a high refractive index and a large wavelength dispersion property in addition, and is preferably used also for an optical element for which a large wavelength dispersion property is required.

The optical material of the present invention has a refractive index $n_d$ and an Abbe number $v_d$ which satisfy a relationship $v_d \leq 213 - 115 \cdot n_d$ ($n_d \geq 1.55$). Accordingly, the optical material of the present invention is preferably used for an application for which the wavelength dispersion property within such a range is required.

An optical element for which such a large wavelength dispersion property is required, may, for example, be a wavelength-selective diffraction element, and as a constituting material therefor, the optical material of the present invention is preferably used.

On that occasion, with a view to further reducing the grating height and improving the efficiency in the production process and the diffraction efficiency, an optical material having a larger wavelength dispersion property is preferably used, and at the refractive index $n_d \geq 1.60$, it is preferred that the Abbe number $v_d \leq 29$, more preferably $v_d \leq 26$.

Here, as one example of an optical element using the optical material of the present invention, a wavelength-selective diffraction element will be described. In the following description, the wavelengths of the incident light will be the wavelength $\lambda 1$ and the wavelength $\lambda 2$ ($\lambda 1 < \lambda 2$).

Figure 1B:
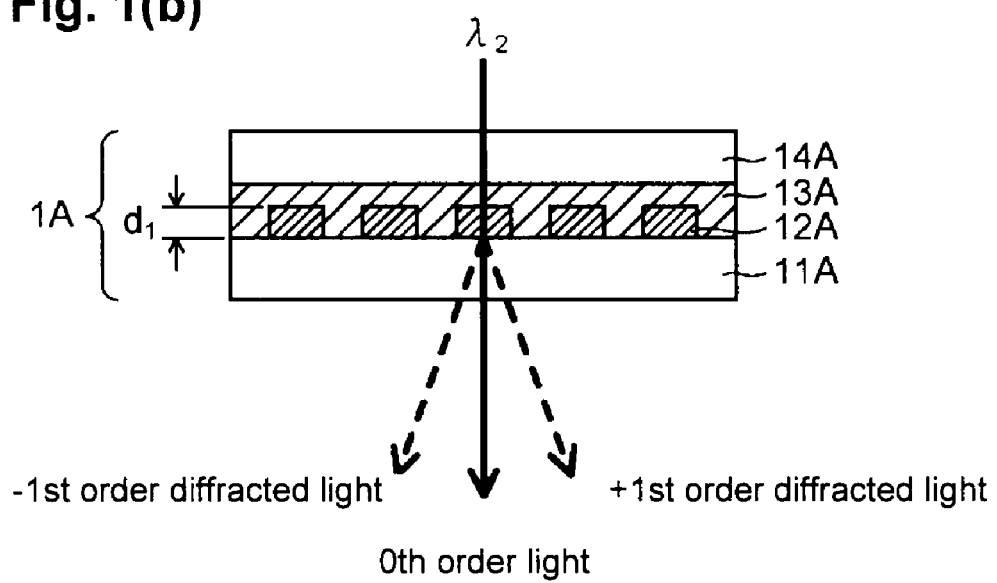

FIGS. 1(a) and 1(b) are cross-sectional views schematically illustrating a wavelength-selective diffraction element according to a first embodiment of the present invention, FIG. 1(a) is a cross-sectional view schematically illustrating the action when a light having a wavelength $\lambda 1$ enters a wavelength-selective diffraction element 1A, and FIG. 1(b) is a cross-sectional view schematically illustrating the action when a light having a wavelength $\lambda 2$ enters the wavelength-selective diffraction element 1A.

In FIGS. 1(a) and 1(b), the wavelength-selective diffraction element 1A comprises a transparent substrate 11A, a diffraction grating 12A comprising a convexoconcave member, formed on the surface of the transparent substrate 11A, and a filling member 13A to fill the convexoconcave portions of the diffraction grating 12A, and the filling member 13A is protected by a transparent substrate 14A formed thereon.

The wavelength-selective diffraction element 1A is formed so that the refractive index of the diffraction grating 12A and the refractive index of the filling member 13A for the light having a wavelength $\lambda 1$ are the same, and the refractive index of the diffraction grating 12A and the refractive index of the filling member 13A for the light having a wavelength $\lambda 2$ are different from each other.

That is, the materials constituting the diffraction grating 12A and the filling member 13A are selected to form the diffraction element 1A so as to satisfy, with respect to the light having a wavelength $\lambda 1$ and the light having a wavelength $\lambda 2$, $n12A(\lambda 1)=n13A(\lambda 1)$ and $n12A(\lambda 2)>n13A(\lambda 2)>0$, where $n12A(\lambda 1)$ is the refractive index of the diffraction grating 12A for the light having a wavelength $\lambda 1$, $n13A(\lambda 1)$ is the refractive index of the filling member 13A for the light having a wavelength $\lambda 1$, $n12A(\lambda 2)$ is the refractive index of the diffraction grating 12A for the light having a wavelength $\lambda 2$, and $n13A(\lambda 2)$ is the refractive index of the filling member 13A for the light having a wavelength $\lambda 2$.

Thus, as shown in FIG. 1(a), a light having a wavelength $\lambda 1$ applied to the wavelength-selective diffraction element 1A goes straight and is transmitted through the diffraction grating 12A without being affected by the diffraction action by the diffraction element 1A, since the refractive indices at the diffraction grating 12A and the filling member 13 are the same. On the other hand, since the refractive index of the diffraction grating 12A and the refractive index of the filling member 13A for a light having a wavelength $\lambda 2$ are different from each other, when the light having a wavelength $\lambda 2$ enters the diffraction grating 12A, as shown in FIG. 1(b), it is diffracted by the refractive index difference, whereby a diffracted light is obtained.

Further, it is possible to adjust the diffraction efficiency by adjusting the height d1 of the diffraction grating 12A, the diffraction shape of the diffraction grating 12A, or the like. Further, it is also possible to control the diffraction angle by adjusting the grating pitch of the diffraction grating 12A.

Accordingly, a wavelength-selective diffraction element 1A which has no function on the light having a wavelength $\lambda 1$ and has a diffraction function only on the light having a wavelength $\lambda 2$, can be obtained.

Here, in the wavelength-selective diffraction element 1A, with a view to reducing the transmission loss by light absorption, either of materials constituting the diffraction grating 12A and the filling member 13A preferably shows normal dispersion within a range of from the wavelength $\lambda 1$ to the wavelength $\lambda 2$, and $n12A(\lambda 1)$, $n13A(\lambda 1)$, $n12A(\lambda 2)$ and $n13A(\lambda 2)$ preferably satisfy the relation of $n12A(\lambda 1)>n12A(\lambda 2)$ and $n13A(\lambda 1)>n13A(\lambda 2)$.

In such a case, $n12A(\lambda 1)=n13A(\lambda 1)>n12A(\lambda 2)>n13A(\lambda 2)$ is satisfied, and the filling member 13A shows a larger wavelength dispersion property (a smaller Abbe number) as compared with the diffraction grating 12A.

As a material constituting such a filling member 13A, the optical material of the present invention can suitably be used.

Now, a wavelength-selective diffraction element 1B shown in FIGS. 2(a) and 2(b) will be described.

Figure 2A:
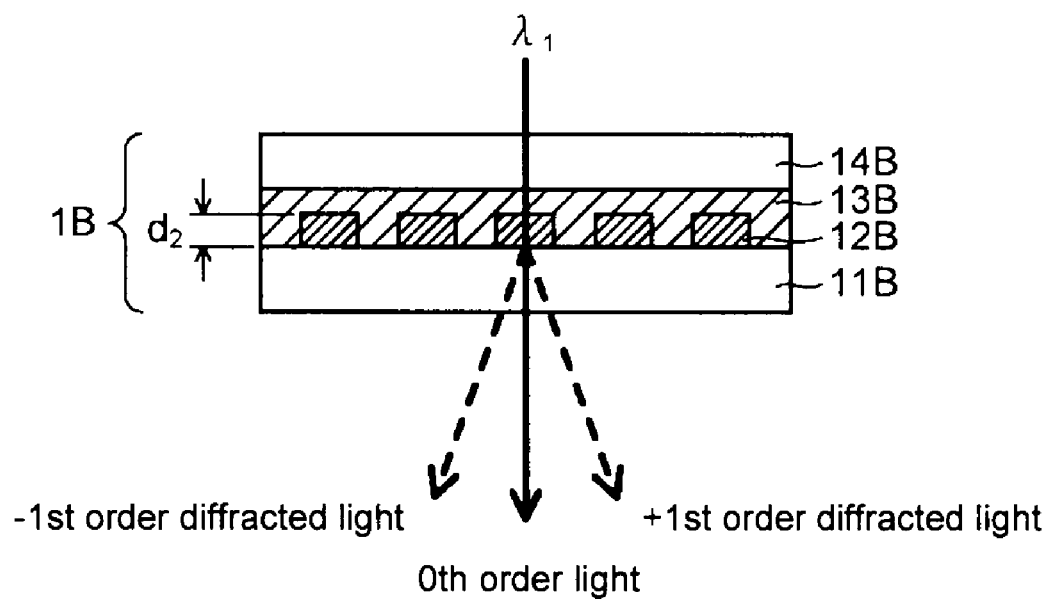
FIGS. 2(a) and 2(b) are cross-sectional views schematically illustrating a wavelength-selective diffraction element according to a second embodiment of the present invention.
Figure 2B:
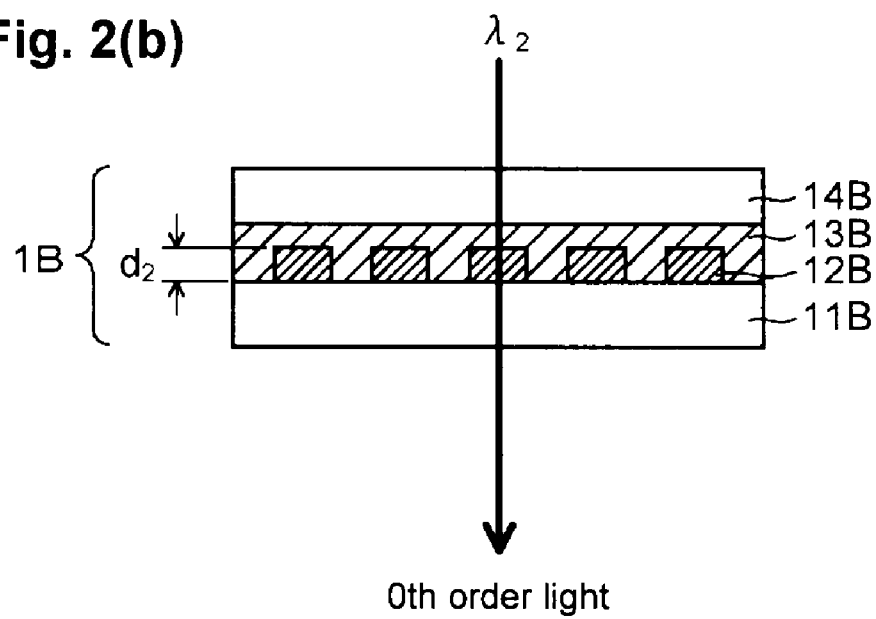

FIGS. 2(a) and 2(b) are cross-sectional views schematically illustrating a wavelength-selective diffraction element according to a second embodiment of the present invention, FIG. 2(a) is a cross-sectional view schematically illustrating the action when a light having a wavelength $\lambda 1$ enters a wavelength-selective diffraction element 1B, and FIG. 2(b) is a cross-sectional view schematically illustrating the action when a light having a wavelength $\lambda 2$ enters the wavelength-selective diffraction element 1B.

In FIGS. 2(a) and 2(b), the wavelength-selective diffraction element 1B comprises a transparent substrate 11B, a diffraction grating 12B comprising a convexoconcave member, formed on the surface of the transparent substrate 11B, and a filling member 13B to fill convexoconcave portions of the diffraction grating 12B, and the filling member 13B is protected by a transparent substrate 14B formed thereon.

The wavelength-selective diffraction element 1B is formed so that the refractive index of the diffraction grating 12B and the refractive index of the filling member 13B for the light having a wavelength $\lambda 1$ are the same, and the refractive index of the diffraction grating 12B and the refractive index of the filling member 13B for the light having a wavelength λ2 are different from each other.

That is, the materials constituting the diffraction grating 12B and the filling member 13B are selected to form the diffraction element 1B so as to satisfy, with respect to the light having a wavelength λ1 and the light having a wavelength λ2, n12B(λ1)>n13B(λ1)>0 and n12B(λ2)=n13B(λ2), where n12B (λ1) is the refractive index of the diffraction grating 12B for the light having a wavelength λ1, n13B (λ1) is the refractive index of the filling member 13B for the light having a wavelength λ1, n12B(λ2) is the refractive index of the diffraction grating 12B for the light having a wavelength λ2, and n13B (λ2) is the refractive index of the filling member 13B for the light having a wavelength λ2.

Accordingly, as shown in FIG. 2(a), the light having a wavelength λ1 which enters the diffraction grating 12B is diffracted by the diffraction grating 12B, and a diffracted light is obtained.

Further, it is possible to control the diffraction angle by adjusting the grating pitch of the diffraction grating 12B. Further, it is possible to adjust the transmission efficiency of the light which goes straight and the diffraction efficiency of the diffracted light by changing the height d2 of the diffraction grating 12B or the diffraction shape of the diffraction grating 12B.

On the other hand, as shown in FIG. 2(b), the light having a wavelength λ2 which enters the diffraction grating 12B goes straight and is transmitted without being diffracted by the diffraction grating 12B.

A wavelength-selective diffraction element 1B which has no function on the light having a wavelength λ1 and has a diffraction function only on the light having a wavelength λ2, can be obtained.

Here, in the wavelength-selective diffraction element 1B, with a view to reducing the transmission loss by light absorption, either of materials constituting the diffraction grating 12B and the filling member 13B shows normal dispersion within a range of from the wavelength λ1 to the wavelength λ2, and n12B(λ1), n13B(λ1), n12B(λ2) and n13B(λ2) preferably satisfy, for example, the relation of n12B(λ1)>n12B (λ2) and n13B(λ1)>n13B(λ2).

In such a case, n12B(λ1)>n13B(λ1)>n12B(λ2)=n13B(λ2) is satisfied, and the diffraction grating 12B shows a larger wavelength dispersion property (a smaller Abbe number) as compared with the filling member 13B.

As a material constituting such a diffraction grating 12B, the optical material of the present invention can suitably be used.

Now, a wavelength-selective diffraction element 1C shown in FIGS. 3(a) and 3(b) will be described.

Figure 3A:
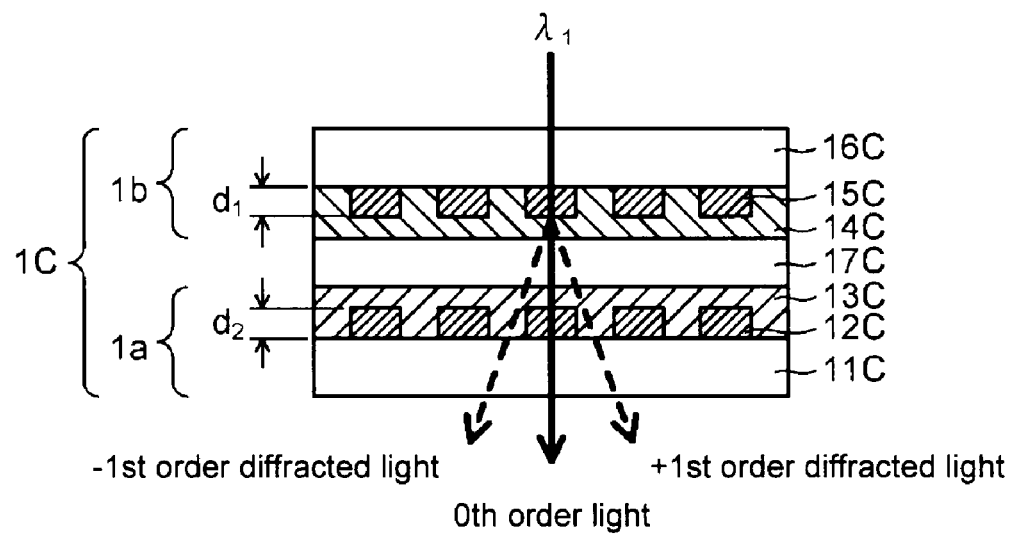
FIGS. 3(a) and 3(b) are cross-sectional views schematically illustrating a wavelength-selective diffraction element according to a third embodiment of the present invention.
Figure 3B:
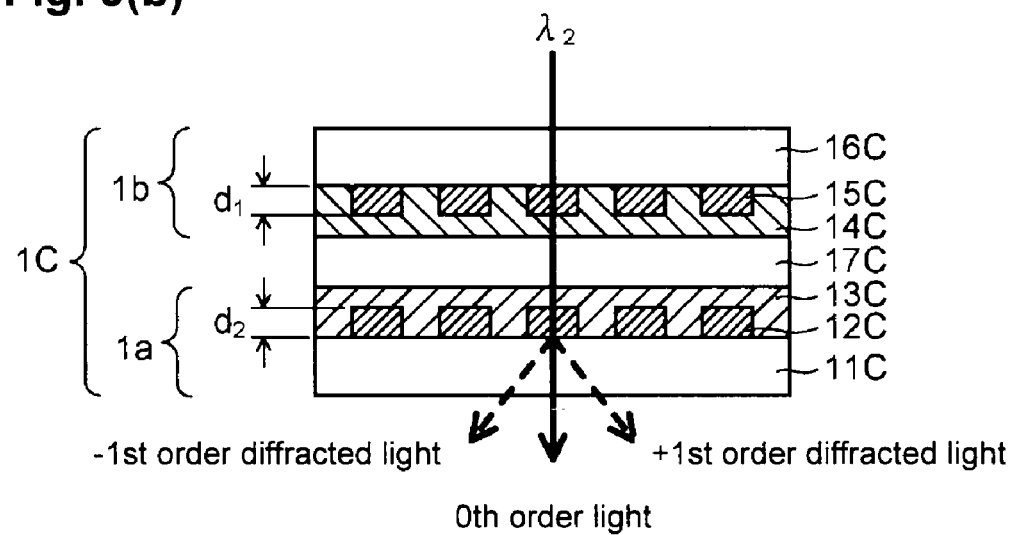

FIGS. 3(a) and 3(b) are cross-sectional views schematically illustrating a wavelength-selective diffraction element according to a third embodiment of the present invention, FIG. 3(a) is a cross-sectional view schematically illustrating the action when a light having a wavelength λ1 enters a wavelength-selective diffraction element 1C, and FIG. 3(b) is a cross-sectional view schematically illustrating the action when a light having a wavelength λ2 enters the wavelength-selective diffraction element 10.

In FIGS. 3(a) and 3(b), the wavelength-selective diffraction element 10 comprises a combination of the wavelength-selective diffraction element 1A according to the first embodiment and the wavelength-selective diffraction element 1B according to the second embodiment, and has a first member 1a comprising a transparent substrate 11C, a diffraction grating 12C comprising a convexoconcave member, formed on the surface of the transparent substrate 110, and a filling member 13C to fill convexoconcave portions of the diffraction grating 12C. Further, above the first member 1a, a second member 1b comprising a transparent substrate 16C, a diffraction grating 15C comprising a convexoconcave member, formed on the surface of the transparent substrate 16C, and a filling member 14C to fill convexoconcave portions of the diffraction grating 15C, is provided, and the first member 1a and the second member 1b are laminated in a state where a transparent substrate 17C is sandwiched between the filling member 13C and the filling member 14C.

Here, in the wavelength-selective diffraction element 1C, the transparent substrate 11C, the diffraction grating 12C and the filling member 13C constituting the first member 1a, and the transparent substrate 17C, respectively correspond to the transparent substrate 11A, the diffraction grating 12A, the filling member 13A and the transparent substrate 14A in the above-described wavelength-selective diffraction element 1A (see FIGS. 1(a) and 1(b)). Further, in the wavelength-selective diffraction element 10, the transparent substrate 16C, the diffraction grating 15C and the filling member 14C constituting the second member 1b, and the transparent substrate 17C respectively correspond to the transparent substrate 11B, the diffraction grating 12B, the filling member 13B and the transparent substrate 14B in the above-described wavelength-selective diffraction element 1B (see FIGS. 2(a) and 2(b)).

The wavelength-selective diffraction element 1C is formed so that the refractive index of the diffraction grating 12C and the refractive index of the filling member 13C for the light having a wavelength λ1 are the same, and the refractive index of the diffraction grating 12C and the refractive index of the filling member 13C for the light having a wavelength λ2 are different from each other.

Further, the wavelength-selective diffraction element 1C is formed so that the refractive index of the diffraction grating 15C and the refractive index of the filling member 14C for the light having a wavelength λ1 are different from each other, and the refractive index of the diffraction grating 15C and the refractive index of the filling member 14C for the light having a wavelength λ2 are the same.

Accordingly, in FIG. 3(a), the light having a wavelength λ1 enters the second member 1b of the wavelength-selective diffraction element 1C, and it is diffracted by the diffraction grating 15C, then it enters the first member 1a, and it is not diffracted by and is transmitted through the diffraction grating 12C. That is, for the light having a wavelength λ1, only the diffraction grating 15C functions as a diffraction grating. On the other hand, in FIG. 3(b), the light having a wavelength λ2 enters the second member 1b of the wavelength-selective diffraction element 1C, and it is transmitted through the diffraction grating 15C, and then it enters the first member 1a, and it is diffracted by the diffraction grating 12C. That is, for the light having a wavelength λ2, only the diffraction grating 12C functions as a diffraction grating.

Accordingly, the wavelength-selective diffraction element 10, which is one element formed by combination of different elements, functions as a diffraction element each independently for two types of wavelengths.

For example, the above wavelength λ1 and wavelength λ2 are regarded as the 405 nm waveband used for BD and the 660 nm waveband used for DVD, respectively.

On that occasion, when the diffraction grating 12A and the filling member 13A of the wavelength-selective diffraction element 1A shown in FIGS. 1(a) and 1(b) satisfy the relation according to the first embodiment, the diffraction element 1A can transmit a light in the 405 nm waveband and can diffract a light in the 660 nm waveband.

Further, since the refractive index in the 785 nm waveband used for CD (compact disk) is close to that in the 660 nm waveband, a wavelength-selective diffraction element which can diffract also a light in the 785 nm waveband can be prepared.

Further, when the diffraction grating 12B and the filling member 13B of the wavelength-selective diffraction element 1B as shown in FIGS. 2(a) and 2(b) satisfy the relation according to the second embodiment, a wavelength-selective diffraction element which can diffract a light in the 405 nm waveband and can transmit a light in the 660 nm waveband can be prepared.

Here, since the refractive index in the 785 nm waveband is close to that in the 660 nm waveband, a wavelength-selective diffraction element which can transmit also a light in the 785 nm waveband can be prepared.

In the above-described wavelength-selective diffraction element, the diffraction efficiency can be adjusted by adjusting the grating height d1 or d2 of the diffraction grating 12A or 12B or by changing the grating shape. Accordingly, a grating height with which a preferred efficiency as an element for generating three beams or a hologram beam splitter may be employed. Further, by the convexoconcave portions of the wavelength-selective diffraction element having a blazed grating shape or a multi-leveled structure stair case grating shape, the diffraction efficiency at a specific order may be increased. Further, the diffraction angle can be adjusted by adjusting the pitch of the diffraction grating, and accordingly a desired diffraction angle can be obtained.

A means employed for conventional element for generated three beams and hologram beam splitter can be applied to the wavelength-selective diffraction element as it is.

Further, the optical material obtained by polymerizing the polymerizable composition of the present invention can be used for an optical element such as a diffraction element other than the above-described diffraction element, or a lens.

Further, when the optical material of the present invention is employed for such an optical element, the means in the process for producing such an optical element is not particularly limited, and for example, the optical material of the present invention may be applied by a known method. Further, the optical material of the present invention can be used also as an adhesive when optical elements are laminated or an optical member is fixed.

Further, the optical material of the present invention and an element using it are excellent in the light resistance against blue laser. Accordingly, the element can be preferably used for an application of an optical pickup device, and can be used for production of an optical head device suitable for large capacity. That is, the optical element using the optical material of the present invention is suitable for an optical head device to record information on an optical recording medium and/or to read information recorded on an optical recording medium, and is particularly suitable for an optical head device for an optical information recording and reading device employing blue laser such as BD. Specifically, it is preferably disposed in the optical path of the laser light in the optical head device. Further, it can also be preferably used for other applications for which a high refractive index resin has been required.

Now, the optical head device of the present invention will be described.

Figure 4:
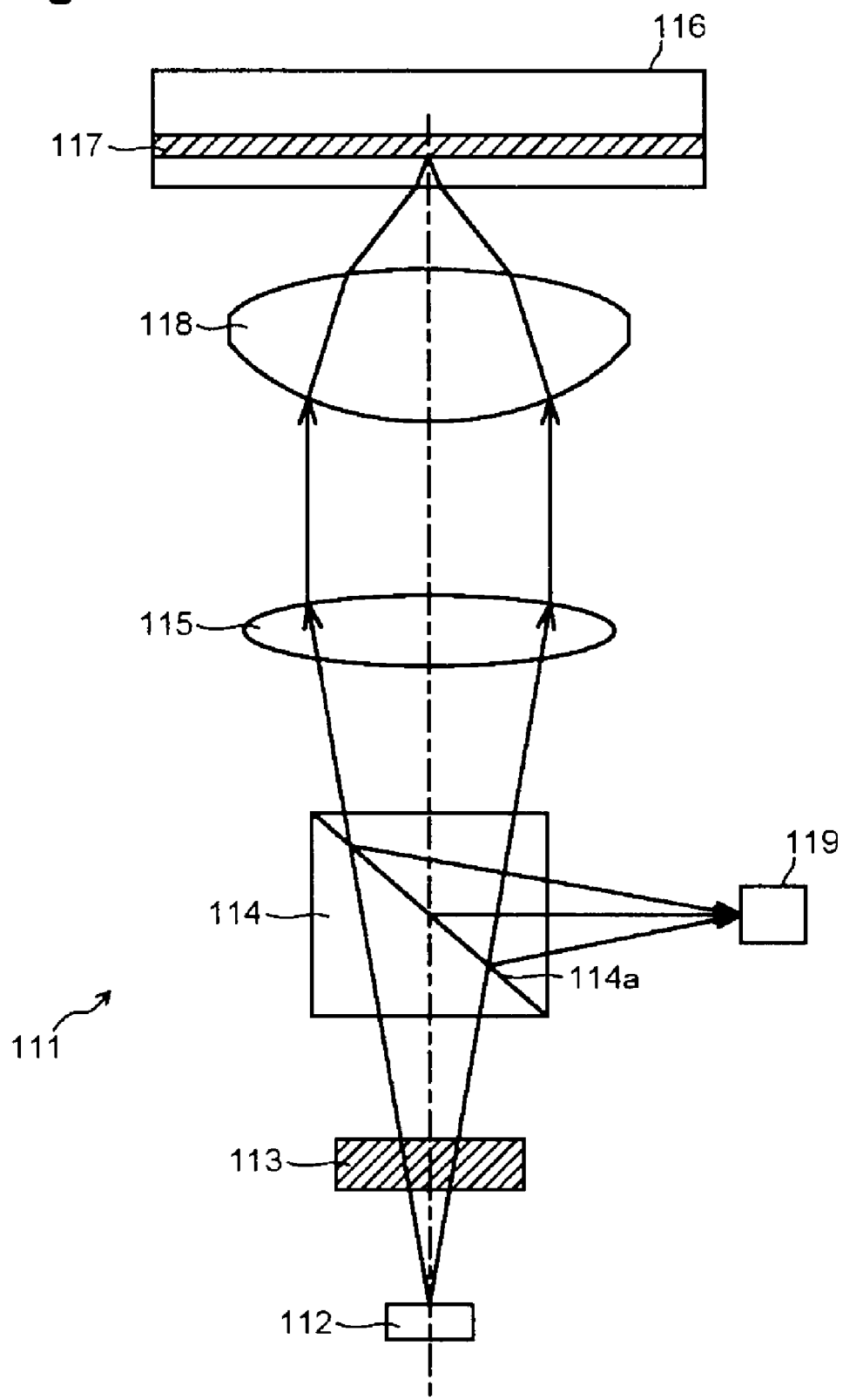
FIG. 4 is a diagram schematically illustrating the constitution of an optical head device according to one embodiment of the present invention.

FIG. 4 is a view schematically illustrating the constitution of an optical head device according to one embodiment of the present invention.

As shown in FIG. 4, an optical head device 111 comprises a light source 112 for emitting laser light, a wavelength-selective diffraction grating 113, a beam splitter 114 which transmits the laser light, a collimator lens 115 to make the laser light to be parallel, an objective lens 118 to focus the laser light on a recording layer 117 of an optical disk 116, and a light detector 119 to detect reflected light from the optical disk 116.

The wavelength-selective diffraction grating 113 is a diffraction grating for generating three beams, and in this embodiment, the above-described wavelength-selective diffraction grating 1B (see FIGS. 2(a) and 2(b)) is applied.

The three beams obtained by the wavelength-selective diffraction grating 113 are used for tracking control when information recorded on BD or the like is read in the optical head device 111.

In FIG. 4, the wavelength-selective diffraction grating 113 is disposed between the light source 112 and the beam splitter 114, but the wavelength-selective diffraction grating 113 should be disposed in the light path between the light source 112 and the objective lens 118, and for example, the wavelength-selective diffraction grating 113 may be disposed between the beam splitter 114 and the objective lens 118. However, as shown in FIG. 4, it is preferred to dispose the wavelength-selective diffraction grating 113 between the light source 112 and the beam splitter 114, whereby reflected light from the optical disk will not be diffracted by the wavelength-selective diffraction grating 113 and the most part reaches the light detector 119, whereby the light utilization efficiency will be increased.

The light source 112 is constituted, for example, by a semiconductor laser diode, and is formed to generate a laser light having a wavelength suitable for the type of the optical disk 116 and to emit it to the wavelength-selective diffraction grating 113. For the light source 112, a common laser light source to be used for a conventional optical head device is used. Specifically, a semiconductor laser is suitably used, but a laser light source other than the semiconductor laser may also be used. The optical material of the present invention, which has excellent light resistance against blue laser, can be suitably used for an optical head device employing blue laser as the light source.

In this embodiment, as the laser lights, laser lights having wavelengths of 405 nm (wavelength $\lambda_1$) and 660 nm (wavelength $\lambda_2$) are used. Further, a plurality of light sources emitting laser lights with wavelengths different from one another may be provided, so that from each light source, laser light is emitted to the wavelength-selective diffraction grating 113.

The wavelength-selective diffraction grating 113 outputs to the beam splitter 114 three beams including light (0th order diffracted light) having laser light with wavelength $\lambda_1$ transmitted without being diffracted, and lights (±1st order diffracted lights) having laser light with wavelength $\lambda_1$ diffracted (see FIG. 2(a)). Further, the wavelength-selective diffraction grating 113 transmits laser light with wavelength $\lambda_2$ and outputs it to the beam splitter 114.

The beam splitter 114 is constituted by a transparent material such as glass or plastic and provided with a reflection surface to reflect the reflected light from the optical disk 116.

The collimator lens 115 is also constituted by a transparent material such as glass or plastic and designed to make incoming laser light to be parallel.

The object lens 118 has a predetermined numerical aperture NA and designed to focus incident light from the collimator lens 115 on a recording layer 117 in the optical disk 116 and to capture reflected light from the recording layer 117.

The light detector 119 comprises a lens, a photodiode, etc. and designed to convert reflected light from the optical disk 116, reflected by the reflection surface of the beam splitter 114, to an electric signal. Further, the light detector 119 receives reflected lights of three beams with wavelength $\lambda_1$, a main beam formed by the 0th order diffracted light and two sub-beams formed by the ±1st order diffracted lights, detects a tracking error based on the difference in quantity of light between the two sub-beams and outputs the detected information to a tracking control section (not shown).

In a case where the optical disk 116 is BD, the optical head device 111 operates as follows.

Firstly, as shown in FIG. 4, with respect to light with wavelength $\lambda_1$ emitted from the light source 12, a part of the emitted light is diffracted by the wavelength-selective diffraction grating 113, whereby from the wavelength-selective diffraction grating 113, lights including 0th order diffracted light and ±1st order diffracted lights are emitted and transmitted through the beam splitter 114 and made to be parallel by the collimator lens 115.

The parallel lights emitted from the collimator lens 115 are focused by the object lens 118 in the form of three beams consisting of 0th order diffracted light and ±1st order diffracted lights, on the information recording track of the optical disk 116. Then, lights reflected by the optical disk 116 are again transmitted from the object lens 118 through the collimator lens 15 and reflected by the beam splitter 114, whereupon the main beam formed by the 0th order diffracted light and the two sub-beams formed by the ±1st order diffracted lights, are focused on the receiving surface of the light detector 119. And, by the light detector 119, a tracking error signal is detected based on the difference in quantity of light between the two sub-beams and output to the tracking control section (not shown).

In a case where the optical disk 116 is DVD, the optical head device 11 operates as follows.

Firstly, as shown in FIG. 4, light with wavelength $\lambda_2$ emitted from the light source 112 is transmitted without being diffracted by the wavelength-selective diffraction grating 113 and then transmitted further through the beam splitter 114 and is made to be parallel by the collimator lens 115. Then, this parallel light is focused by the object lens 118 on the information recording track of the optical disk 116. And, light reflected by the optical disk 116 is again transmitted through the object lens 118 and the collimator lens 115, reflected by the beam splitter 114 and then focused on the receiving surface of the light detector 119.

As described in the foregoing, by using the optical element applying the optical material of the present invention obtained by curing the polymerizable composition containing the polymerizable compound of the present invention, it is possible to constitute a highly reliable optical head device suitable for a large capacity. It should be mentioned that the present invention is not limited to the above-described embodiments, and various modifications may be made within a range not to depart from the concept of the present invention.

Now, the present invention will be described in detail with reference to Examples of the present invention and Comparative Examples. However, it should be understood that the present invention is by no means restricted to such specific Examples.

Now, Examples for preparation of the compounds of the present invention will be described. However, it should be understood that preparation of the compounds of the present invention are not limited to such specific Examples.

Example 1 for Preparation of Polymerizable Compound

The following polymerizable compound A was prepared via compounds (A-1), (A-2) and (A-3) in accordance with the method shown by the following preparation scheme:

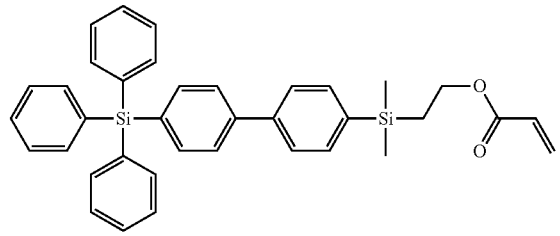

(A)

Preparation Example 1

Example for Preparation of Compound (A)

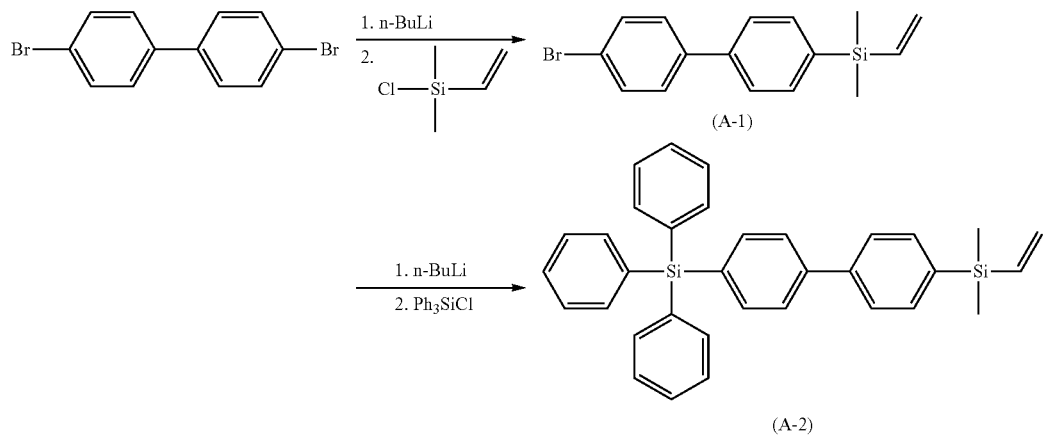

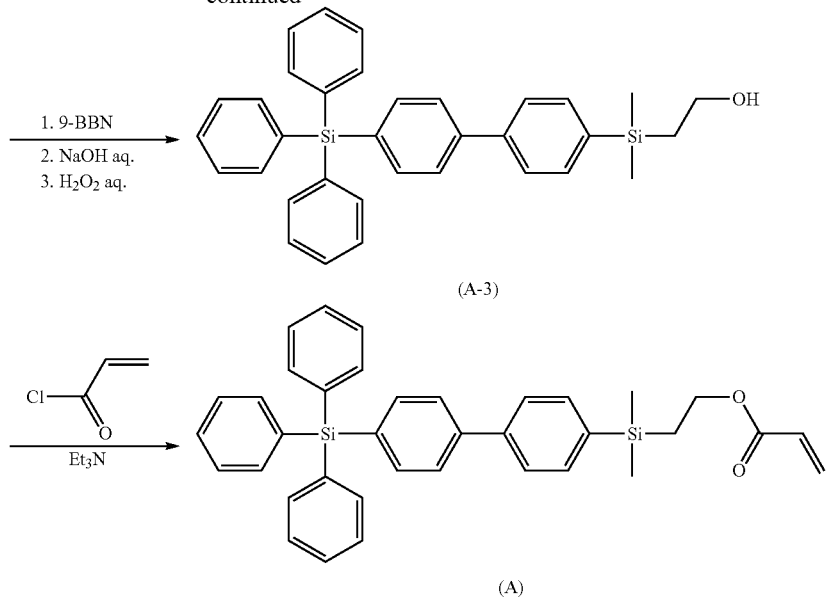

(A-3)

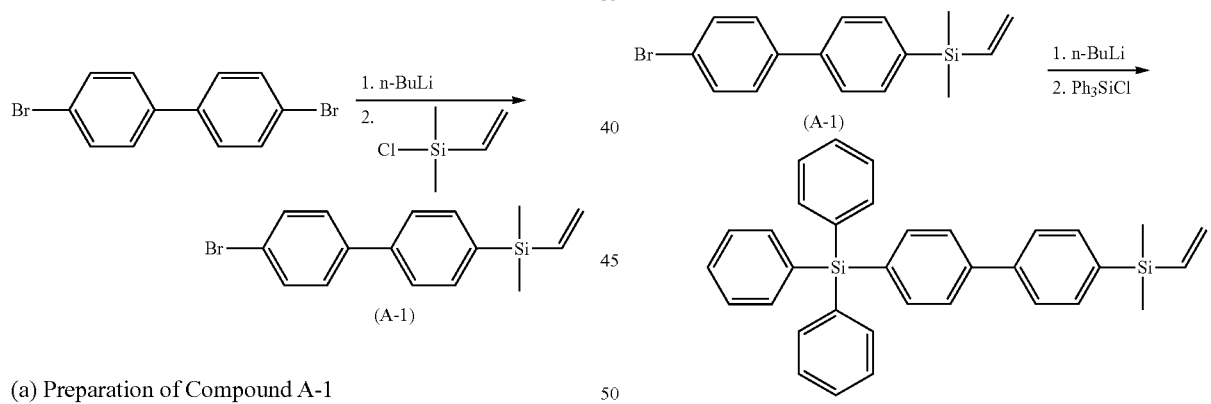

(A)

Now, the respective reactions in the above preparation scheme for polymerizable compound A will be described in detail below.

Example 1-1

Preparation of Compound (A-1)

(a) Preparation of Compound A-1

In a nitrogen atmosphere, to 1 L of dehydrated tetrahydrofuran (hereinafter referred to as THF), 21.0 g (67.3 mmol) of 4,4'-dibromobiphenyl was dissolved and stirred, and then, the solution was cooled to −74° C., and 40.3 ml (67.3 mmol) of a n-butyllithium hexane solution having a concentration of 1.67 mol/L was slowly dropwise added over a period of about 30 minutes, followed by stirring for one hour at −74° C. Then, 11.0 ml (80.9 mmol) of chlorodimethylvinylsilane was dropwise added over a period of 10 minutes, followed by stirring for one hour at −74° C., and the temperature was returned to room temperature, followed by stirring for one hour. Salt water and ethyl acetate were added to extract an organic layer, which was sufficiently dried over magnesium sulfate, and then the solvent was distilled off. Purification by column chromatography with dichloromethane and hexane (dichloromethane:hexane=1:9) was carried out to obtain 19.9 g of compound A-1 which was a white solid in a state containing impurities. The yield was 93.6%.

Example 1-2

Preparation of Compound (A-2)

(b) Preparation of Compound A-2

In a nitrogen atmosphere, 19.9 g (62.9 mmol) of compound A-1 was dissolved in 300 ml of dehydrated THF, and the solution was cooled to −74° C., followed by stirring. Then, 41.5 ml (69.3 mmol) of a n-butyllithium hexane solution having a concentration of 1.67 mol/L was slowly dropwise added over a period of 30 minutes. After reaction at −74° C. for one hour, 24.1 g (82.0 mmol) of triphenylchlorosilane dissolved in 200 mL of THF was slowly dropwise added over a period of about 20 minutes. Then, the mixture was held at −74° C. for one hour, followed by reaction at room temperature for one hour. Then, salt water and ethyl acetate were added to extract an organic layer, which was sufficiently dried over magnesium sulfate, and then the solvent was distilled off. 1 L of ethanol was added to the obtained solid, followed by stirring at 65° C. and washing, and solids insoluble in ethanol at room temperature were collected by filtration to obtain 21.9 g of white solid compound A-2. The yield was 70.1%.

Example 1-3

Preparation of Compound (A-3)

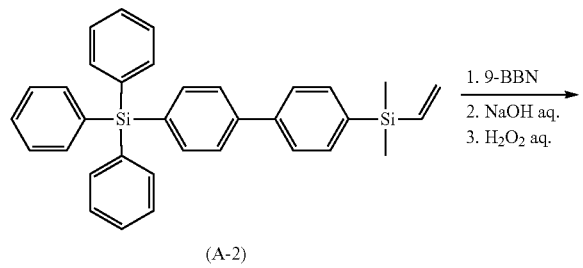

(c) Preparation of Compound A-3

21.9 g (44.2 mmol) of compound A-2 was dissolved in 200 ml of dehydrated THF, and 114.8 ml (57.4 mmol) of a 9-BBN THF solution having a concentration of 0.5 mol/L was dropwise added over a period of about 20 minutes in an ice bath in a nitrogen atmosphere, and the temperature was raised to 65° C., followed by stirring for 3 hours. Then, 30 ml of a 2.5N sodium hydroxide aqueous solution was dropwise added in an ice bath over a period of 30 minutes, and then 100 ml of a 30% hydrogen peroxide solution was dropwise added in an ice bath over a period of 30 minutes. Salt water and ethyl acetate were added to extract an organic layer, which was sufficiently dried over magnesium sulfate, and the solvent was distilled off. Purification by column chromatography with ethyl acetate and hexane (ethyl acetate:hexane=1:3) was carried out, and then recrystallization with hexane was carried out to obtain 11.1 g of white solid compound A-3. The yield was 54.1%.

In the above formula, 9-BBN represents 9-borabicyclo [3.3.1]nonane.

Example 1-4

Preparation of Compound (A)

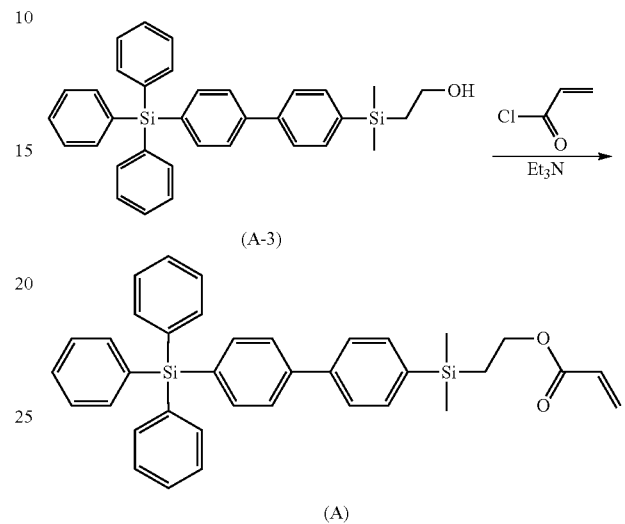

(d) Preparation of Compound A 11.1 g (21.6 mmol) of compound A-3 and 3.59 ml (25.9 mmol) of triethylamine were dissolved in 300 ml of dehydrated THF, followed by stirring. 2.14 ml (25.9 mmol) of acryloyl chloride was dropwise added in an ice bath in a nitrogen atmosphere over a period of about 5 minutes. Diluted hydrochloric acid and ethyl acetate were added to extract an organic layer, which was sufficiently dried over magnesium sulfate, and the solvent was distilled off. Purification by column chromatography with ethyl acetate and hexane (ethyl acetate:hexane=1:15) was carried out, and the solvent was distilled off, and then the obtained transparent viscous material was subjected to recrystallization with 100 ml of hexane and about 2 ml of dichloromethane (dichloromethane was added to such an extent that the viscous material formed at low temperature was dissolved) to obtain 7.0 g of white solid compound A. The yield was 57.1%.

Spectral data of 1H-NMR spectrum (solvent: $CDCl_3$, internal standard: tetramethylsilane (TMS)) of polymerizable compound A are as follows. δ (ppm): 0.36 (6H, s), 1.31 (2H, t), 4.28 (2H, t), 5.77 (1H, m), 6.08 (1H, m), 6.33 (1H, m), 7.38-7.66 (23H, m). The obtained compound A had a melting point of 67° C.

Example 2 for Preparation of Polymerizable Compound

Preparation Example 2

Example for Preparation of Compound (B)

Compound B was prepared in the same manner as in Preparation Example 1 except that allylchlorodimethylsilane was used instead of chlorodimethylvinylsilane and borane was used instead of 9-BBN.

(B)

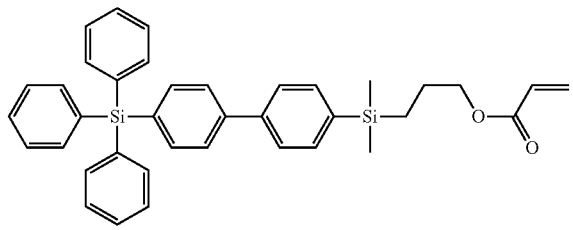

Spectral data of 1H-NMR spectrum (solvent: CDCl₃, internal standard: tetramethylsilane (TMS)) of polymerizable compound B are as follows. δ (ppm): 0.31 (6H, s), 0.80 (2H, t), 1.70 (2H, m), 4.12 (2H, t), 5.81 (1H, m), 6.11 (1H, m), 6.39 (1H, m), 7.37-7.79 (23H, m). The obtained compound B had a melting point of 116° C.

Example 3 for Preparation of Polymerizable Compound

Polymerizable compound C was prepared via compounds (C-1) and (C-2) in accordance with the method shown by the following preparation scheme.

(C)

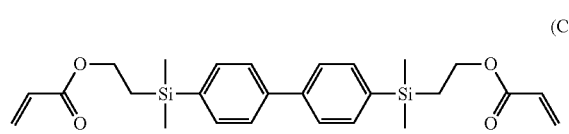

Preparation Example 3

Example for Preparation of Compound (C)

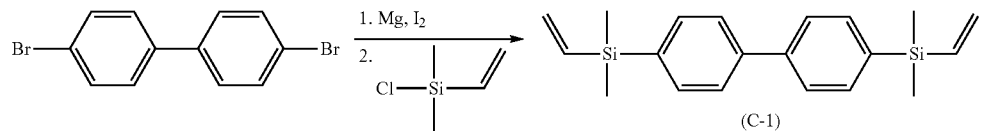

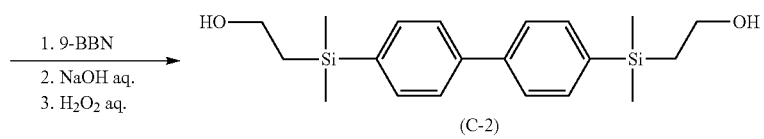

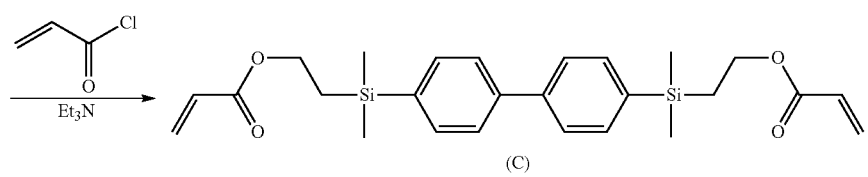

Now, the respective reactions in the above preparation scheme for the polymerizable compound C will be described in detail below.

Example 3-1

Preparation of Compound (C-1)

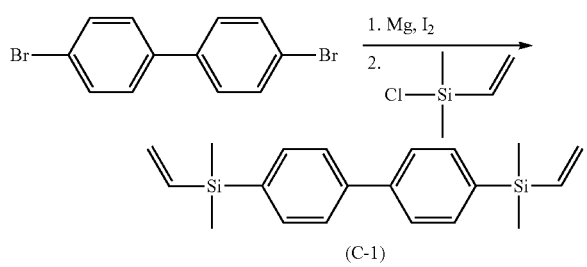

(a) Preparation of Compound C-1

2.54 g (105.8 mmol) of magnesium and about 0.2 g of iodine were stirred in 20 ml of dehydrated tetrahydrofuran in a nitrogen atmosphere, and about 20 ml of a solution having 15.0 g (48.1 mmol) of 4,4'-dibromobiphenyl dissolved in 400 ml of dehydrated THF was dropwise added to the above dehydrated tetrahydrofuran, followed by heating by a heat gun to initiate Grignard reaction. After the initiation of the reaction, the rest of the solution was dropwise added over a period of about 30 minutes, followed by stirring with heating at 65° C. for 12 hours. Then, 14.4 ml (105.9 mmol) of chlorodimethylvinylsilane was dropwise added over a period of about 10 minutes, followed by stirring at 65° C. for one hour. A saturated ammonium chloride solution and ethyl acetate were added to extract an organic layer, which was sufficiently dried over magnesium sulfate, and the solvent was distilled off. Purification by column chromatography with dichloromethane and hexane (dichloromethane:hexane=1:19) was carried out to obtain 10.8 g of transparent liquid compound C-1. The yield was 69.7%.

Example 3-2

Preparation of Compound (C-2)

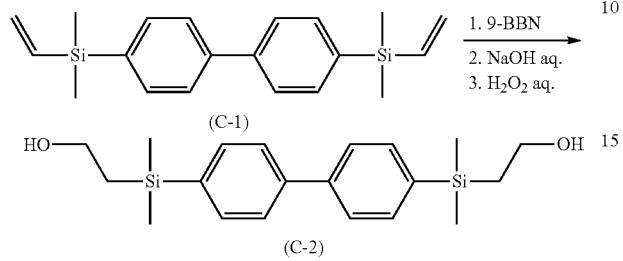

(b) Preparation of Compound C-2

10.8 g (33.5 mmol) of compound C-1 was dissolved in 100 ml of dehydrated THF, and 161 ml (80.5 mmol) of a 9-BBN THF solution having a concentration of 0.5 mol/L was dropwise added in an ice bath in a nitrogen atmosphere over a period of about 20 minutes, and the temperature was raised to 65° C., followed by stirring for 12 hours. Then, 40 ml of a 2.2N sodium hydroxide aqueous solution was dropwise added in an ice bath over a period of 30 minutes, and then 120 ml of a 30% hydrogen peroxide solution as dropwise added in an ice bath over a period of 30 minutes. Salt water and ethyl acetate were added to extract an organic layer, which was sufficiently dried over magnesium sulfate, and the solvent was distilled off. Purification by column chromatography with ethyl acetate and hexane (ethyl acetate:hexane=1:1) was carried out to obtain 9.0 g of white solid compound C-2. The yield was 75%.

Example 3-3

Preparation of Compound (C)

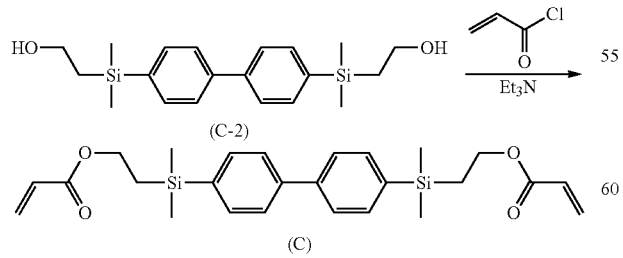

(c) Preparation of Compound C 9.0 g (25 mmol) of compound C-2 and 8.3 ml (60 mmol) of triethylamine were dissolved in 300 ml of dehydrated THF and stirred. 5.0 ml (60 mmol) of acryloyl chloride was dropwise added in an ice bath in a nitrogen atmosphere over a period of about 10 minutes. Diluted hydrochloric acid and ethyl acetate were added to extract an organic layer, which was sufficiently dried over magnesium sulfate, and the solvent was distilled off. Purification by column chromatography with ethyl acetate and hexane (ethyl acetate:hexane=1:7) was carried out to obtain 4.0 g of transparent and colorless liquid compound C. The yield was 62%.

Spectral data of $^1$H-NMR spectrum (solvent: CDCl$_3$, internal standard: tetramethylsilane (TMS)) of polymerizable compound C were as follows. δ (ppm): 0.31 (12H, s), 1.32 (4H, t), 4.28 (4H, t), 5.77 (2H, m), 6.06 (2I, m), 6.34 (2H, m), 7.59 (8H, m).

Example 4 for Preparation of Polymerizable Compound

Preparation Example 4

Example for Preparation of Compound (D)

Compound D was prepared in the same manner as in Preparation Example 1 except that allylchlorodimethylsilane was used instead of chlorodimethylvinylsilane and borane was used instead of 9-BBN.

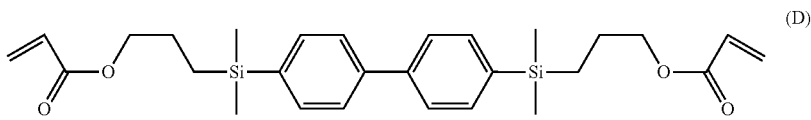

Spectral data of 1H-NMR spectrum (solvent: CDCl$_3$, internal standard: tetramethylsilane (TMS)) of polymerizable compound D are as follows. δ (ppm): 0.32 (12H, s), 0.81 (4H, t), 1.71 (4H, m), 4.11 (4H, t), 5.81 (2H, m), 6.11 (2H, m), 6.39 (2H, m), 7.58 (8H, m). The obtained compound D had a melting point of 65° C.

Example 5 for Preparation of Polymerizable Compound

Polymerizable compound E was prepared via compounds (E-1), (E-2) and (E-3) in accordance with the method shown by the following preparation scheme.

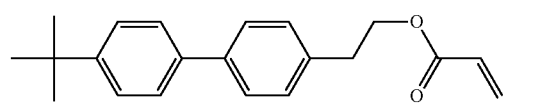

Preparation Example 5

Example for Preparation of Compound (E)

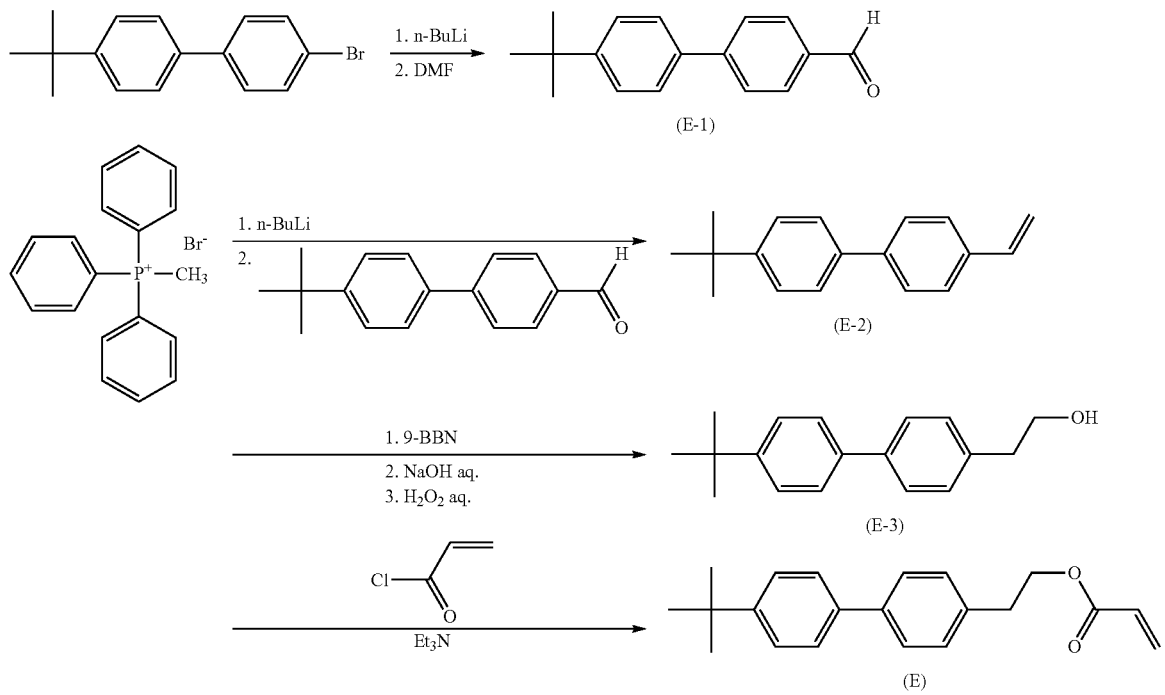

Now, the respective reactions in the above preparation scheme for polymerizable compound E will be described in detail below.

Example 5-1

Preparation of Compound (E-1)

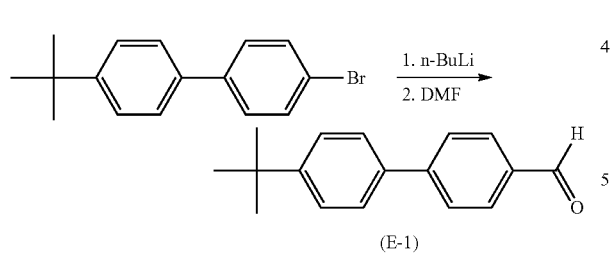

(a) Preparation of Compound E-1

5.0 g (17.3 mmol) of 4-bromo-4'-tert-butylbiphenyl was dissolved in 150 ml of dehydrated THF in a nitrogen atmosphere, and the solution was cooled to −74° C., followed by stirring. Then, 11.9 ml (19.0 mmol) of a n-butyllithium hexane solution having a concentration of 1.6 mol/L was slowly dropwise added over a period of about 30 minutes. After reaction at −74° C. for 30 minutes, 2.7 ml (34.9 mmol) of DMF was dropwise added over a period of about 5 minutes. Then, the reaction mixture was held at −74° C. for 30 minutes, followed by reaction at room temperature for 30 minutes. Then, salt water and ethyl acetate were added to extract an organic layer, which was sufficiently dried over magnesium sulfate, and the solvent was distilled off. Purification by column chromatography with ethyl acetate and hexane (ethyl acetate:hexane=1:9) was carried out to obtain 3.3 g of compound E-1. The yield was 80.1%.

In the above formula, DMF represents N,N-dimethylformamide.

Example 5-2

Preparation of Compound (E-2)

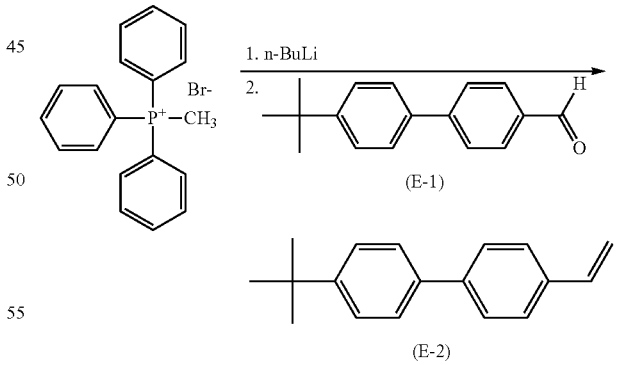

(b) Preparation of Compound E-2

8.9 g (24.9 mmol) of triphenylphosphonium bromide was added to 150 ml of dehydrated THF in a nitrogen atmosphere, and the mixture was cooled to −74° C., followed by stirring. Then, 15.6 ml (25.0 mmol) of a n-butyllithium hexane solution having a concentration of 1.6 mol/L was slowly dropwise added over a period of about 30 minutes. After reaction in an ice bath for 30 minutes, 3.3 g of E-1 (13.9 mmol) dissolved in 10 ml of dehydrated THF was dropwise added over a period of about 15 minutes. Then, the mixture was maintained in an ice bath for 30 minutes, followed by reaction at room temperature for 30 minutes. Then, salt water and ethyl acetate were added to extract an organic layer, which was sufficiently dried over magnesium sulfate, and the solvent was distilled off. Purification by column chromatography with ethyl acetate and hexane (ethyl acetate:hexane=1:6) was carried out to obtain 3.2 g of compound E-2. The yield was 97.8%.

Example 5-3

Preparation of Compound (E-3)

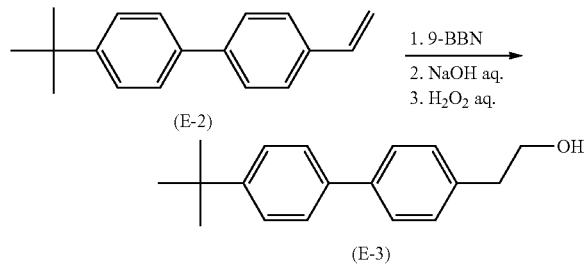

(c) Preparation of Compound E-3

3.2 g (13.6 mmol) of compound E-2 was dissolved in 150 ml of dehydrated THF, and 36.3 ml (18.2 mmol) of a 9-BBN THF solution having a concentration of 0.5 mol/L was dropwise added in an ice bath in a nitrogen atmosphere over a period of about 15 minutes, and the temperature was raised to 65° C., followed by stirring for 12 hours. Then, 20 ml of a 1.3N sodium hydroxide aqueous solution was dropwise added in an ice bath over a period of 10 minutes, and then 30 ml of a 30% hydrogen peroxide solution was dropwise added in an ice bath over a period of 20 minutes. Salt water and ethyl acetate were added to extract an organic layer, which was sufficiently dried over magnesium sulfate, and the solvent was distilled off. Purification by column chromatography with ethyl acetate and hexane (ethyl acetate:hexane=1:3) was carried out to obtain 2.9 g of compound E-3. The yield was 84.4%.

Example 5-4

Preparation of Compound (E)

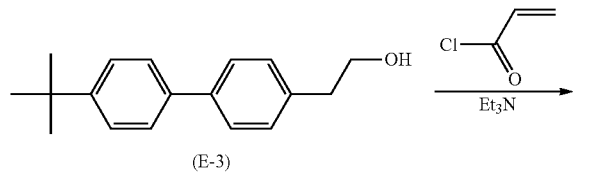

(d) Preparation of Compound E 2.9 g (11 mmol) of compound E-3 and 1.8 ml (13 mmol) of triethylamine were dissolved in 200 ml of dehydrated THF, followed by stirring. 1.1 ml (13 mmol) of acryloyl chloride dissolved in 10 ml of dehydrated THF was dropwise added in an ice bath in a nitrogen atmosphere over a period of about 10 minutes. Diluted hydrochloric acid and ethyl acetate were added to extract an organic layer, which was sufficiently dried over magnesium sulfate, and the solvent was distilled off. Purification by column chromatography with ethyl acetate and hexane (ethyl acetate:hexane=1:9) was carried out to obtain 2.6 g of white solid compound E. The yield was 74%.

Spectral data of 1H-NMR spectrum (solvent: $CDCl_3$, internal standard: tetramethylsilane (TMS)) of polymerizable compound E are as follows. δ (ppm): 1.36 (9H, s), 3.02 (2H, t), 4.40 (2H, t), 5.83 (1H, m), 6.12 (1H, m), 6.40 (1H, m), 7.28-7.54 (8H, m). The obtained compound E had a melting point of 67° C.

Example 6 for Preparation of Polymerizable Compound

Polymerizable compound F was prepared via compounds (F-1) and (F-2) in accordance with the method shown by the following preparation scheme.

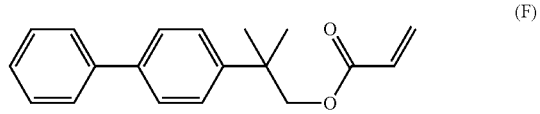

Preparation Example 6

Example for Preparation of Compound (F)

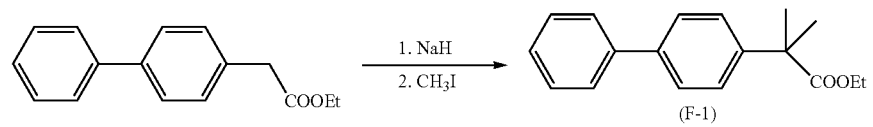

-continued

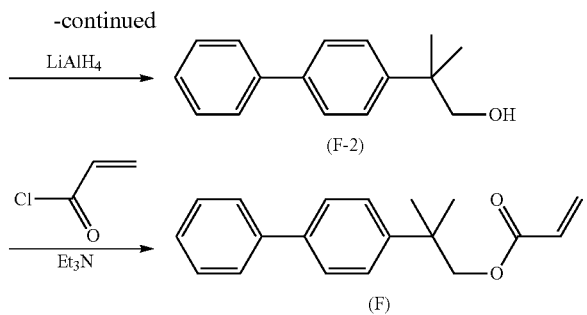

Now, the respective reactions in the above preparation scheme for polymerizable compound F will be described in detail below.

Example 6-1

Preparation of Compound (F-1)

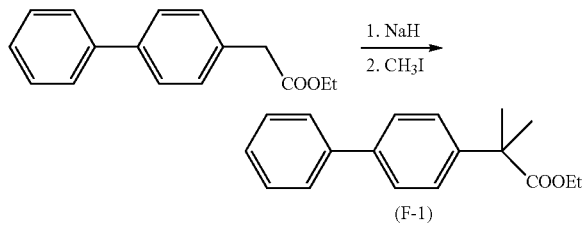

(a) Preparation of Compound F-1

5.6 g (151 mmol) of sodium hydride was mixed with 300 ml of dehydrated THF, and 14.5 g (60.4 mmol) of ethyl 4-biphenylacetate dissolved in 50 ml of dehydrated THF was slowly dropwise added in an ice bath in a nitrogen atmosphere over a period of about 20 minutes. After stirring at room temperature for one and a half hours, 25 g (17.6 mmol) of iodomethane was dropwise added in an ice bath, followed by reaction at room temperature for 4 hours. A saturated ammonium chloride solution and ethyl acetate were added in an ice bath to extract an organic layer, which was sufficiently dried over magnesium sulfate, and the solvent was distilled off. Purification by column chromatography with ethyl acetate and hexane (ethyl acetate:hexane=1:7) was carried out to obtain 14.4 g of transparent and colorless liquid compound F-1. The yield was 88.9%.

Example 6-2

Preparation of Compound (F-2)

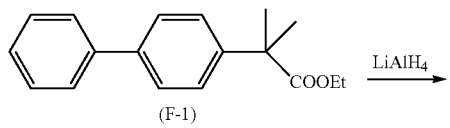

-continued

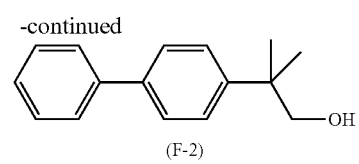

(b) Preparation of Compound F-2

4.1 g (108 mmol) of lithium aluminum hydride was mixed with 250 ml of dehydrated THF in an ice bath in a nitrogen atmosphere, and 14.4 g of F-1 (53.7 mmol) dissolved in 50 ml of dehydrated THF was slowly dropwise added over a period of about 30 minutes. After stirring at room temperature for 8 hours, 40 ml of a saturated ammonium chloride solution was dropwise added, and a mixed solvent of 174 ml of ethyl acetate, 20 ml of methanol and 6 ml of triethylamine was slowly dropwise added in an ice bath. The solid component was removed by filtration, and an organic layer was distilled off to about 100 ml. Salt water and ethyl acetate were added to extract an organic layer, which was sufficiently dried over magnesium sulfate, and the solvent was distilled off. Purification by column chromatography with dichloromethane was carried out to obtain 10.0 g of white solid compound F-2. The yield was 82.4%.

Example 6-3

Preparation of Compound (F)

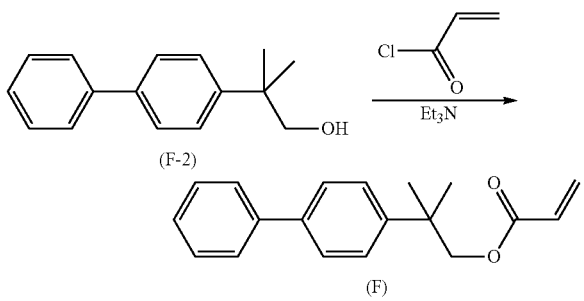

(c) Preparation of Compound F 10.0 g (44.2 mmol) of compound F-2 and 7.3 ml (52.0 mmol) of triethylamine were dissolved in 300 ml of dehydrated THF, followed by stirring. 4.4 ml (53.2 mmol) of acryloyl chloride dissolved in 10 ml of dehydrated THF was dropwise added in an ice bath in a nitrogen atmosphere over a period of about 15 minutes. Diluted hydrochloric acid and ethyl acetate were added to extract an organic layer, which was sufficiently dried over magnesium sulfate, and the solvent was distilled off. Purification by column chromatography with ethyl acetate and hexane (ethyl acetate:hexane=1:6) was carried out to obtain 9.8 g of white solid compound F. The yield was 79.1%.

Spectral data of 1H-NMR spectrum (solvent: CDCl$_3$, internal standard: tetramethylsilane (TMS)) of polymerizable compound F are as follows. δ (ppm): 1.42 (6H, s), 4.25 (2H, s), 5.80 (1H, m), 6.10 (1H, m), 6.36 (1H, m), 7.31-7.61 (9H, m). The obtained compound F had a melting point of 43° C.

Example 7 for Preparation of Polymerizable Compound

Polymerizable compound G was prepared via compounds (G-1), (G-2) and (G-3) in accordance with the method shown by the following preparation scheme.

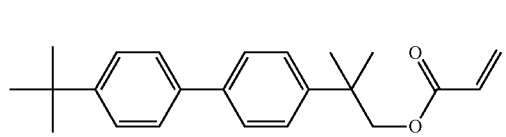

(G)

Preparation Example 7

Example for Preparation of Compound (G)

Now, the respective reactions in the above preparation scheme for polymerizable compound G will be described in detail below.

Example 7-1

Preparation of Compound (G-1)

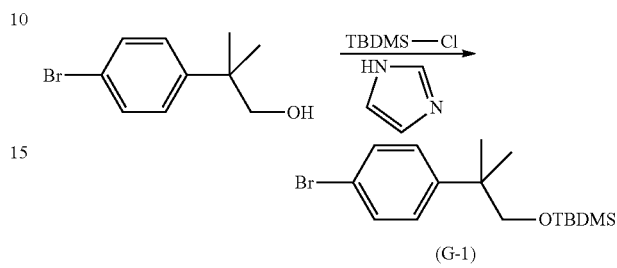

(a) Preparation of Compound G-1

8.1 g (35.4 mmol) of 2-(4-bromophenyl)-2-methylpropan-1-ol, 6.4 g (42.4 mmol) of tert-butyldimethylsilyl chloride and 2.9 g (42.6 mmol) of imidazole were dissolved in 100 ml of DMF, followed by stirring at room temperature for one hour. Then, salt water and ethyl acetate were added to extract an organic layer, which was sufficiently dried over magnesium sulfate, and the solvent was distilled off. Purification by column chromatography with ethyl acetate and hexane (ethyl

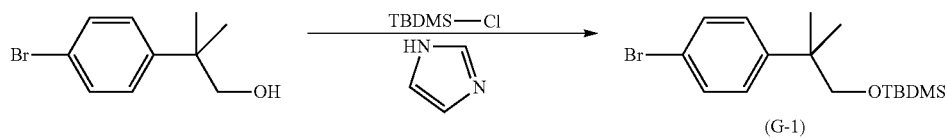

(G-1)

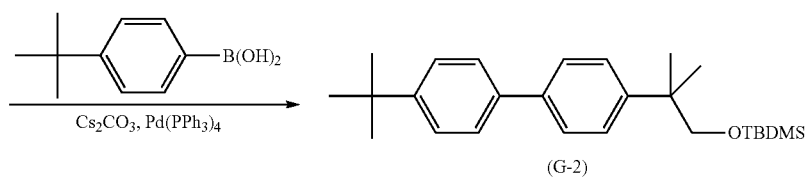

(G-2)

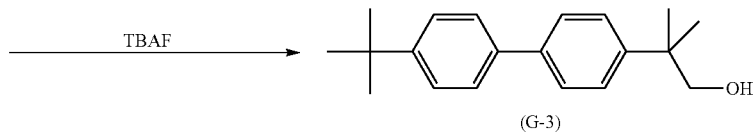

(G-3)

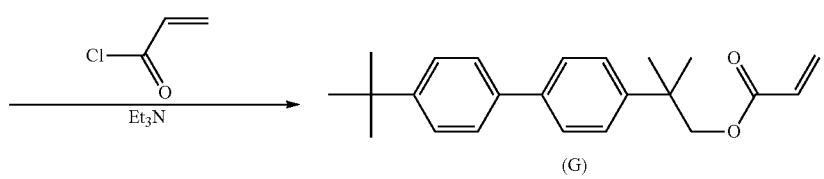

(G)

acetate:hexane=1:9) was carried out to obtain 9.3 g of transparent and colorless liquid compound G-1. The yield was 76.9%. In the above formula, TBDMS represents a tert-butyldimethylsilyl group.

Example 7-2

Preparation of Compound (G-2)

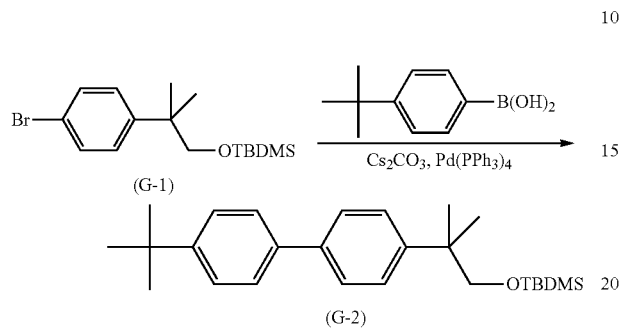

(b) Preparation of Compound G-2

8.0 g (23.3 mmol) of compound G-1, 5.0 g (28.1 mmol) of 4-tert-butylphenyl boronic acid and 24.4 g (74.8 mmol) of cesium carbonate were dissolved in 250 ml of toluene and 150 ml of water, followed by stirring, and 1 g of tetrakistriphenylphosphine palladium(0) was added, followed by stirring at 70° C. for 3 days. Then, the temperature was returned to room temperature, and salt water and ethyl acetate were added to extract an organic layer, which was sufficiently dried over magnesium sulfate, and the solvent was distilled off. Purification by column chromatography with ethyl acetate and hexane (ethyl acetate:hexane=1:9) was carried out to obtain 8.6 g of transparent and colorless liquid compound G-2. The yield was 92.6%.

Example 7-3

Preparation of Compound (G-3)

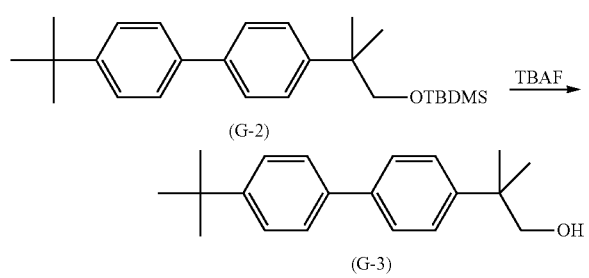

(c) Preparation of Compound G-3

8.6 g (21.7 mmol) of compound G-2 was dissolved in 150 ml of THF, and 8.2 g (26.0 mmol) of tetrabutylammonium fluoride was further added, followed by stirring at room temperature for 30 minutes. Salt water and ethyl acetate were added to extract an organic layer, which was sufficiently dried over magnesium sulfate, and the solvent was distilled off. Purification by column chromatography with ethyl acetate and hexane (ethyl acetate:hexane=1:3) was carried out to obtain 5.5 g of white solid compound G-3. The yield was 90.0%.

In the above formula, TBAF represents tetrabutylammonium fluoride.

Example 7-4

Preparation of Compound (G)

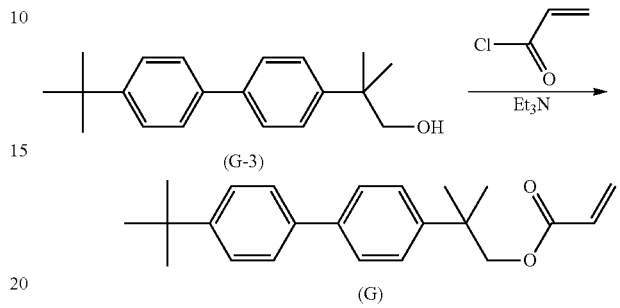

(d) Preparation of Compound G 5.5 g (19.5 mmol) of compound G-3 and 3.2 ml (23.1 mmol) of triethylamine were dissolved in 200 ml of dehydrated THF, followed by stirring. 1.9 ml (23.0 mmol) of acryloyl chloride dissolved in 10 ml of dehydrated THF was dropwise added in an ice bath in a nitrogen atmosphere over a period of about 15 minutes. Diluted hydrochloric acid and ethyl acetate were added to extract an organic layer, which was sufficiently dried over magnesium sulfate, and the solvent was distilled off. Purification by column chromatography with ethyl acetate and hexane (ethyl acetate:hexane=1:8) was carried out to obtain 2.9 g of white solid compound G. The yield was 44.3%.

Spectral data of 1H-NMR spectrum (solvent: $CDCl_3$, internal standard: tetramethylsilane (TMS)) of polymerizable compound G were as follows. δ (ppm): 1.36 (9H, s), 1.42 (6H, s), 4.24 (2H, s), 5.80 (1H, m), 6.09 (1H, m), 6.35 (1H, m), 7.31-7.54 (8H, m). The obtained compound G had a melting point of 56° C.

<Polymerization of Photocurable Composition and Evaluation of Refractive Index>

Example 1

To 100 parts by weight of compound A, 0.5 part by weight of a photopolymerization initiator (manufactured by Ciba Specialty Chemicals, tradename: "IC184") was added, followed by stirring under heating until the mixture became uniform thereby to obtain photocurable polymerizable composition A.

Then, a pair of glass plates were bonded at four corner portions by an adhesive having glass beads with a diameter of 10 μm incorporated, to prepare a glass cell with a glass distance of 10 μm. The above photocurable polymerizable composition A was injected in the liquid state into this glass cell, and then, to the glass plates, ultraviolet rays were applied from a perpendicular direction for 2 minutes to obtain cell A. The illuminance of a high pressure mercury lamp employed was 100 mW/cm² at a wavelength of 365 nm. Then, one of the pair of glass plates was removed by a cutter to obtain a test specimen A having an optical material i.e. a cured film attached on one side (hereinafter referred to as a cured film). Using a prism coupler (manufactured by Metricon, tradename: "Model 2010"), the refractive indices at wavelengths of 404 nm, 633 nm and 791 nm were measured at room temperature and found to be 1.686, 1.626 and 1.615, respectively, and thus the cured film was found to be a cured film having a high refractive index.

Then, based on the refractive indices at the three wavelengths, parameters A, B and C of the Cauchy's dispersion formula $(n(\lambda)=A+B/\lambda^2+C/\lambda^4)$ were obtained from fitting by means of a least square method, whereby refractive indices at from 400 to 800 nm were led, and based thereon, the refractive index $n_d$ at 589 nm and the Abbe number $v_d$ were calculated, whereby $n_d$ was 1.632 and $v_d$ was 21.6. From the obtained Abbe number $v_d$, the cured film was found to be a cured film having a large wavelength dispersion property.

Examples 2 to 7

Photocurable polymerizable compositions B, C, D, E, F and G were obtained in the same manner as in Example 1

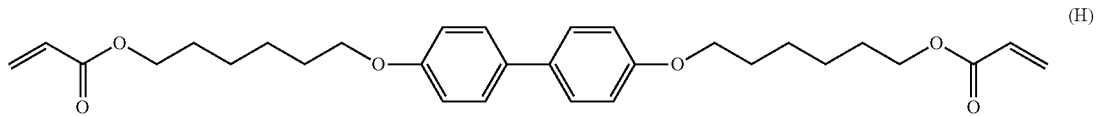

(H)

except that compounds B, C, D, E, F and G were used instead of compound A. Cells B, C, D, E, F and G were obtained by using such polymerizable compositions B, C, D, E, F and G, and one of glass plates in each cell was removed to prepare test specimens B, C, D, E, F and G. The refractive indices of test specimens B, C, D, E, F and G were measured at room temperature to calculate $n_d$ and $v_d$ and as a result, the refractive indices $n_d$ at 589 nm of the respective test specimens were 1.640, 1.570, 1.567, 1.581, 1.600 and 1.571, and the Abbe numbers $v_d$ were 20.3, 26.3, 28.6, 25.9, 25.4 and 26.3, respectively. All the cured films were confirmed to be cured films of a resin having a high refractive index and a large wavelength dispersion property.

<Polymerization of Photocurable Composition and Evaluation of Light Resistance>

Example 8

A glass cell was prepared in the same manner as in Example 1 except that glass plates each having an antireflective film coating on one surface, were used, so that the surfaces opposite to the coating surfaces faced each other, and that the diameter of glass beads incorporated in the adhesive was changed to 20 μm. To 100 parts by weight of compound A, 0.5 part by weight of "IC184" (tradename, manufactured by Ciba Specialty Chemicals) was added as a photoinitiator, followed by stirring under heating until the mixture became uniform to obtain liquid photocurable composition A. The obtained composition was injected in the liquid state into the glass cell, and ultraviolet rays were applied for 2 minutes from a perpendicular direction to the glass plates to obtain laminate A. Here, the illuminance of high pressure mercury lamp employed was 100 mW/cm² at a wavelength of 365 nm.

To the above laminate A, blue LD light with oscillation wavelength of 406 nm was applied at 80° C. until 7 W·hour/mm². The transmittances were measured before and after the application, whereby the transmittance change $\Delta T_{PD}$ was less than 1%. Here, $\Delta T_{LD}$=(blue LD light transmittance before application)−(blue LD light transmittance after application).

Examples 9 to 14

Laminates B, C, D, E, F and G were prepared in the same manner as in Example 8 except that compounds B, C, D, E, F and G were used instead of compound A. The light resistance test was carried out in the same manner as in Example 8 to measure $\Delta T_{PD}$ of laminates B, C, D, E, F and G, whereby $\Delta T_{LD}$ of all laminates was less than 1%, whereby high light resistance was confirmed.

Comparative Example 1

In the same manner as in Example 1 except that the following compound H was used instead of compound A, cell H was prepared, and test specimen H having a cured film attached was obtained. The refractive index was measured at room temperature and as a result, the refractive index at 589 nm was 1.573, and the Abbe number $v_d$ was 28.7.

Then, laminate H was obtained in the same manner as in Example 8 and the transmittance was measured and as a result, the transmittance change $\Delta T_{PD}$ was 4%.

Comparative Example 2

In the same manner as in Example 1 except that the following compound I was used instead of compound A, cell I was prepared, and test specimen I having a cured film attached was obtained. The refractive index was measured at room temperature and as a result, the refractive index at 589 nm was 1.607, and the Abbe number $v_d$ was 25.4.

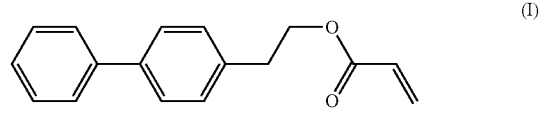

(I)

Then, laminate I was obtained in the same manner as in Example 8 and the transmittance was measured and as a result, the transmittance change $\Delta T_{PD}$ was 58%.

Comparative Example 3

In the same manner as in Example 1 except that the following compound J was used instead of compound A, cell J was prepared, and test specimen J having a cured film attached was obtained. The refractive index was measured at room temperature and as a result, the refractive index at 589 nm was 1.596, and the Abbe number $v_d$ was 26.1.

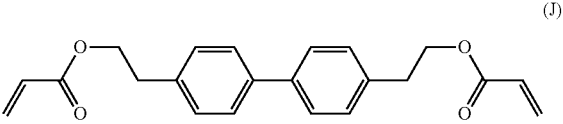

(J)

Then, laminate J was obtained in the same manner as in Example 8 and the transmittance was measured and as a result, the transmittance change $\Delta T_{PD}$ was 6%.

Comparative Example 4

In the same manner as in Example 1 except that the following compound K was used instead of compound A, cell K was prepared, and test specimen K having a cured film attached was obtained. The refractive index was measured at room temperature and as a result, the refractive index at 589 nm was 1.651, and the Abbe number $v_d$ was 20.3.

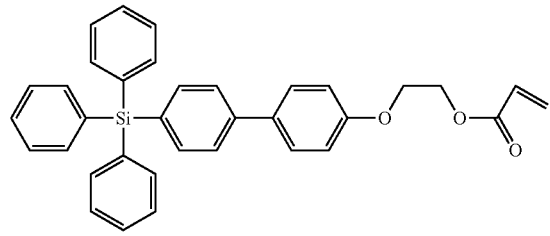

(K)

Then, laminate K was obtained in the same manner as in Example 8 and the transmittance was measured and as a result, the transmittance change $\Delta T_{PD}$ was 7%.

The refractive index $n_d$ and the Abbe number $v_d$ of each of cured films in Examples 1 to 7, obtained by using polymerizable compounds A to G, and the transmittance change $\Delta T_{PD}$ of each of laminates A to G in Examples 8 to 14 obtained by using polymerizable compounds A to G are shown in Table 1. Further, the refractive index $n_d$ and the Abbe number $v_d$ of each of cured films in Comparative Examples 1 to 4 obtained by using compounds H to K and the transmittance change $\Delta T_{PD}$ of each of laminates H to K obtained by using compounds H to K are shown in Table 1.

TABLE 1

|  | Compound | Refractive index of resin nd | Abbe number $v_d$ | Transmittance change $\Delta T_{LD}$ |
|---|---|---|---|---|
| Ex. | Compound A | 1.632 | 21.6 | <1% |
|  | Compound B | 1.640 | 20.3 | <1% |
|  | Compound C | 1.570 | 26.3 | <1% |
|  | Compound D | 1.567 | 28.6 | <1% |
|  | Compound E | 1.581 | 25.9 | <1% |
|  | Compound F | 1.600 | 25.4 | <1% |
|  | Compound G | 1.571 | 26.3 | <1% |
| Comp. Ex. | Compound H | 1.573 | 28.7 | 4% |
|  | Compound I | 1.607 | 25.4 | 58% |
|  | Compound J | 1.596 | 26.1 | 6% |
|  | Compound K | 1.651 | 20.3 | 7% |

As evident from Table 1, the cured film obtained by using the polymerizable compound of the present invention was confirmed to have a high refractive index and a large wavelength dispersion property and have excellent light resistance as well. Here, the transmittance change $\Delta T_{PD}$ is preferably at most 1%.

Comparative Examples 5 to 8

In the same manner as in Example 1 except that the following compounds L, M, N and O were used instead of compound A, cells L to 0 were prepared, and test specimens L to 0 having a cured film attached were obtained.

Here, compounds L, M, N and O are compounds as disclosed in Patent Document 3.

The refractive indices of the cured films of test specimens L to 0 were measured at room temperature and as a result, the refractive indices at 589 nm were 1.622, 1.616, 1.609 and 1.599, respectively, and the Abbe numbers $v_d$ were 26.4, 27.2, 27.8 and 29.1, respectively.

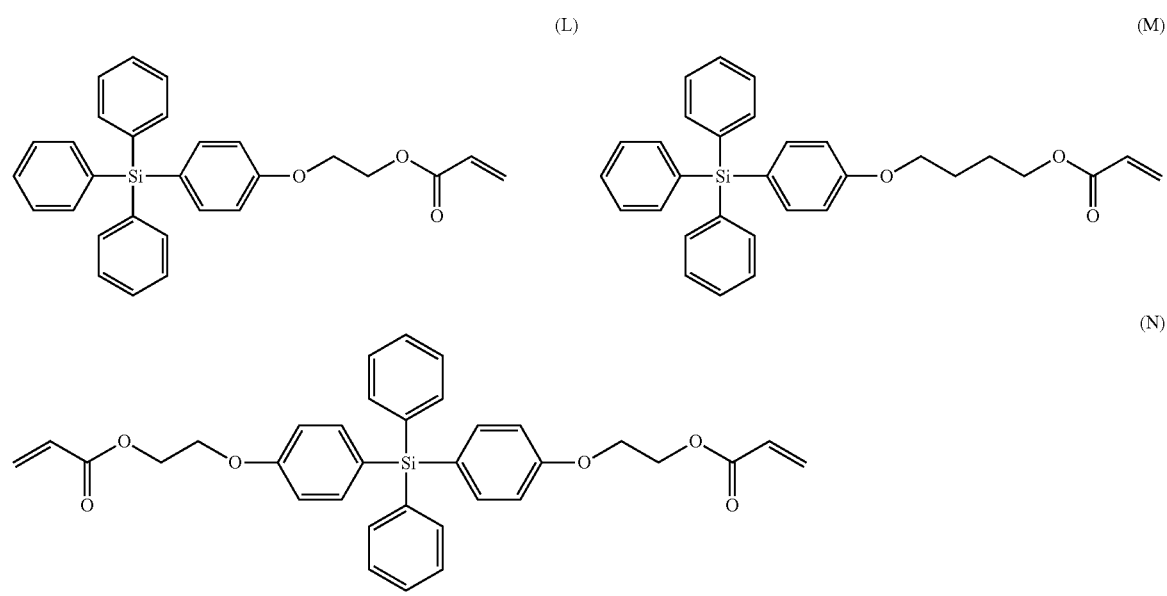

(O)

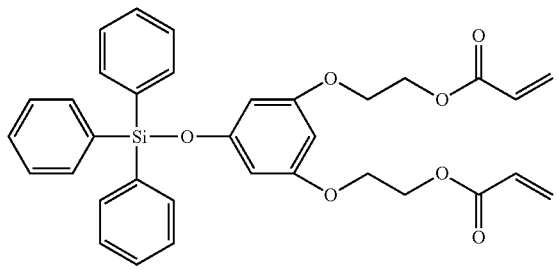

Figure 5:
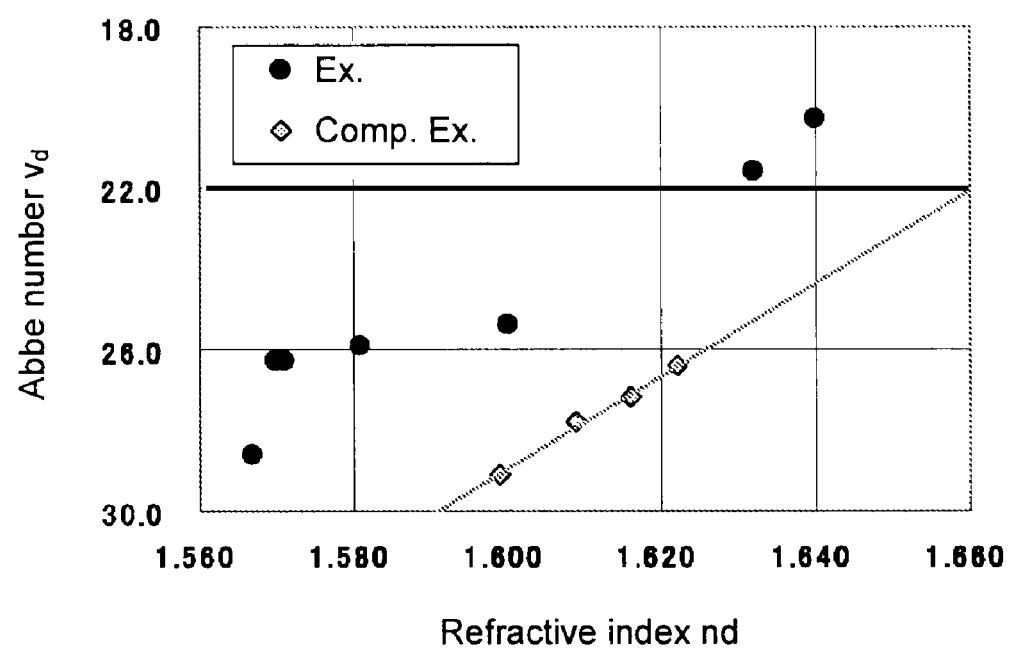
FIG. 5 is a diagram illustrating the relation between the refractive index $n_d$ and the Abbe number $v_d$ of each cured film (optical material).

The relation between the refractive index $n_d$ and the Abbe number $v_d$ of each of cured films obtained from compounds A to G in Examples 1 to 7 and each of cured films obtained from compounds L to O in Comparative Examples 5 to 7 is shown in FIG. 5.

As shown in FIG. 5, each of the cured films obtained from the polymerizable compounds of the present invention was confirmed to have a small Abbe number $v_d$ even in a high refractive index region and has a large wavelength dispersion property as compared with the cured films obtained by using the polymerizable compounds in Comparative Examples.

As described above, the polymerizable biphenylene compound of the present invention was confirmed to be a material having all of high light resistance, high refractive index and large wavelength dispersion property.

The entire disclosure of Japanese Patent Application No. 2010-138624 filed on Jun. 17, 2010 including specification, claims, drawings and summary is incorporated herein by reference in its entirety.

Reference Symbols

1A to 1C: wavelength-selective diffraction element, 11A, 14A, 11B, 14B, 11C, 16C and 17C: transparent substrate, 12A, 12B, 12C and 15C: diffraction grating, 13A, 13B, 13C and 14C: filling member, 1a: first member, 1b: second member, 111: optical head device, 112: light source, 113: wavelength-selective diffraction element, 114: beam splitter, 114a: beam splitter layer, 115: collimator lens, 116: optical disk, 117: recording layer, 118: objective lens, 119: light detector

What is claimed is:

1. A polymerizable compound represented by the following formula (1):

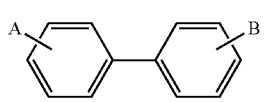 (1)

wherein A is a hydrogen atom or a group selected from the following formulae (2) to (5):

$V_w H_{(3-w)} C-$ (2)

$Ph_x Y_{(3-x)} Si-$ (3)

$J-(CH_2)_{m1}-CH_l(CH_3)_{(2-l)}-$ (4)

$J-(CH_2)_{n1}-SiPh_{p1}(CH_3)_{(2-p1)}-$ (5);

B is a group selected from the following formulae (6) and (7):

$J-(CH_2)_{m2}-CH_k(CH_3)_{(2-k)}-$ (6)

$J-(CH_2)_{n2}-SiPh_{p2}(CH_3)_{(2-p2)}-$ (7);

w is an integer of from 0 to 3;

V is a methyl group or an ethyl group, provided that when w is from 2 to 3, a plurality of V's may be different groups, x is an integer of from 0 to 3, Y is a group selected from a methyl group, a cyclohexyl group, a tert-butyl group, a sec-butyl group and an isopropyl group, provided that when x is 0 or 1, a plurality of Y's may be different groups, J is a group selected from $CH_2=CR-COO-$, an epoxy group, a vinyl group and a vinyl ether group, R is a hydrogen atom or a methyl group, l is an integer of from 0 to 1, k is an integer of from 0 to 2, provided that when A is a hydrogen atom, k is not 2, each of $m_1$ and $m_2$ which are independent of each other, is from 0 to 12, each of $n_1$ and $n_2$ which are independent of each other, is from 1 to 12, and each of $p_1$ and $p_2$ which are independent of each other, is from 0 to 2;

provided that some or all of hydrogen atoms in the substituent V in the formula (2), the phenyl group and the substituent Y in the formula (3) and the alkylene group in the formulae (4) to (7) may be substituted by a methyl group, a methoxy group or a fluorine atom, and some or all of hydrogen atoms in the biphenyl group or the biphenylene group may be substituted by a methyl group, a methoxy group or a fluorine atom.

2. The polymerizable compound according to claim 1, wherein A is a group represented by the formula (3).

3. The polymerizable compound according to claim 2, wherein A is a triphenylsilyl group.

4. The polymerizable compound according to claim 1, wherein A is a triphenylsilyl group, and B is a group represented by the formula (7).

5. The polymerizable compound according to claim 1, wherein A is a group represented by the formula (5), and B is a group represented by the formula (7).

6. The polymerizable compound according to claim 1, wherein when B is a group represented by the formula (6), k=0.

7. The polymerizable compound according to claim 1, wherein when B is a group represented by the formula (7), $p_2=0$.

8. The polymerizable compound according to claim 1, wherein A is a tert-butyl group.

9. The polymerizable compound according to claim 1, wherein each of $m_1$ and $m_2$ which are independent of each other, is from 1 to 2, and each of $n_1$ and $n_2$ which are independent of each other, is from 1 to 3.

10. A polymerizable composition comprising the polymerizable compound as defined claim 1.

11. An optical material obtained by curing the polymerizable composition as defined in claim 10.

12. An optical element using the optical material as defined in claim 11.

13. An optical head device using the optical element as defined in claim 12.

* * * * *